US007955559B2

(12) United States Patent
Joshi et al.

(10) Patent No.: US 7,955,559 B2
(45) Date of Patent: Jun. 7, 2011

(54) NANOELECTRONIC ELECTROCHEMICAL TEST DEVICE

(75) Inventors: Kanchan A. Joshi, Emeryville, CA (US); Ray Radtkey, Oakland, CA (US); Christian Valcke, Orinda, CA (US)

(73) Assignee: Nanomix, Inc., Emeryville, CA (US)

( * ) Notice: Subject to any disclaimer, the term of this patent is extended or adjusted under 35 U.S.C. 154(b) by 176 days.

(21) Appl. No.: 12/146,320

(22) Filed: Jun. 25, 2008

(65) Prior Publication Data

US 2009/0084678 A1     Apr. 2, 2009

Related U.S. Application Data

(63) Continuation-in-part of application No. 11/274,747, filed on Nov. 15, 2005, now abandoned.

(60) Provisional application No. 60/937,256, filed on Jun. 26, 2007, provisional application No. 60/604,293, filed on Nov. 13, 2004.

(51) Int. Cl.
*D01F 9/12* (2006.01)
(52) U.S. Cl. .................. 422/68.1; 977/723; 361/226
(58) Field of Classification Search .................. 422/68.1; 977/721–723; 361/226
See application file for complete search history.

(56) References Cited

U.S. PATENT DOCUMENTS

| | | | |
|---|---|---|---|
| 4,935,345 A | 6/1990 | Guilbeau et al. | |
| 6,962,823 B2 | 11/2005 | Empedocles et al. | |
| 2002/0117659 A1 | 8/2002 | Lieber et al. | |
| 2003/0041438 A1 | 3/2003 | Wei et al. | |
| 2003/0077642 A1 | 4/2003 | Fritsch et al. | |
| 2003/0113713 A1 | 6/2003 | Glezer et al. | |
| 2003/0134433 A1 | 7/2003 | Gabriel et al. | |
| 2004/0065970 A1 | 4/2004 | Blanchet-Fincher | |
| 2004/0146958 A1* | 7/2004 | Bae et al. | 435/14 |
| 2004/0200734 A1 | 10/2004 | Co et al. | |
| 2005/0230270 A1* | 10/2005 | Ren et al. | 205/777.5 |
| 2006/0040381 A1* | 2/2006 | Zhao et al. | 435/287.9 |
| 2006/0115640 A1 | 6/2006 | Yodh et al. | |
| 2006/0141469 A1 | 6/2006 | Rossier et al. | |
| 2007/0208243 A1* | 9/2007 | Gabriel et al. | 600/347 |
| 2008/0185295 A1 | 8/2008 | Briman et al. | |

FOREIGN PATENT DOCUMENTS

| | | |
|---|---|---|
| WO | WO 2008/045799 | 4/2008 |
| WO | WO 2009/017911 | 2/2009 |

OTHER PUBLICATIONS

Zhao et al, "Synthesis and Properties of a Water-Soluble Single-Walled Carbon Nano-tube Poly(m-aminobenzene sulfonic acid) Graft Copolymer", Adv Funct Mater (2004) vol. 14, No. 1 pp. 71-76.*
US Office Action dated Feb. 25, 2008 issued in U.S. Appl. No. 11/274,747 (P038X3).
US Examiner Interview Summary dated May 28, 2008 issued in U.S. Appl. No. 11/274,747 (P038X3).
US Office Action Final dated Feb. 11, 2009 issued in U.S. Appl. No. 11/274,747 (P038X3).

(Continued)

*Primary Examiner* — Thomas L Dickey
(74) *Attorney, Agent, or Firm* — Weaver Austin Villeneuve & Sampson LLP

(57) ABSTRACT

Nanoelectronic devices for the detection and quantification of biomolecules are Provided. In certain embodiments, the devices are configured to detect and measure blood glucose levels. Also provided are methods of fabricating nanoelectronic devices for the detection of biomolecules.

26 Claims, 10 Drawing Sheets

3 linker 1 carbon SWNT

OTHER PUBLICATIONS

US Notice of Abandonment dated Sep. 11, 2009 issued in U.S. Appl. No. 11/274,747 (P038X3).
PCT International Search Report dated Sep. 9, 2008 issued in PCT/US07/080603 (P022WO).
PCT International Preliminary Report on Patentability and Written Opinion dated Apr. 7, 2009 issued in PCT/US07/080603 (P022WO).
PCT International Search Report dated Jan. 2, 2009 issued in PCT/US2008/68228 (P046WO).
PCT International Preliminary Report on Patentability and Written Opinion dated Jan. 5, 2010 issued in PCT/US2008/68228 (P046WO).

* cited by examiner

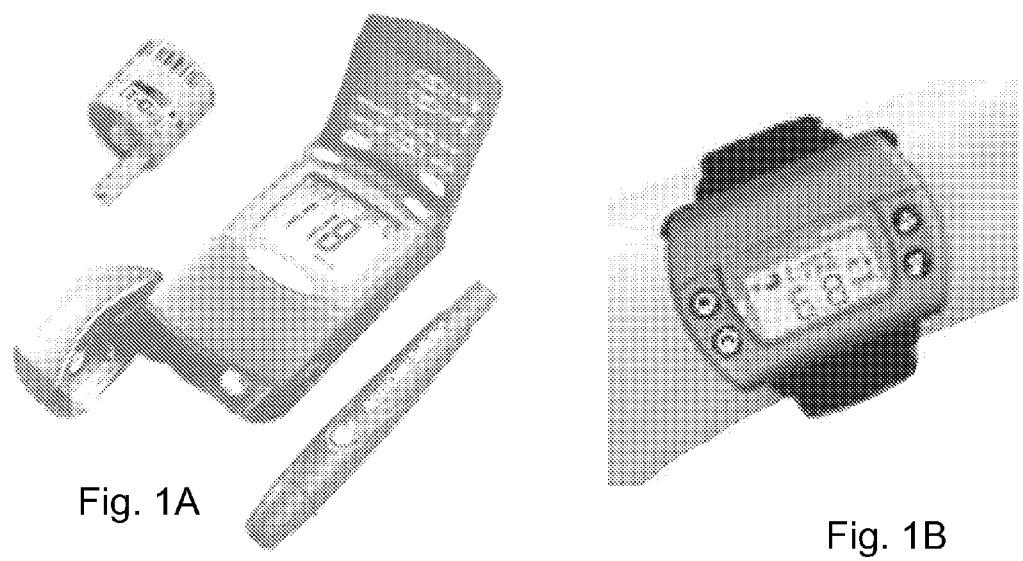
Fig. 1A
Fig. 1B
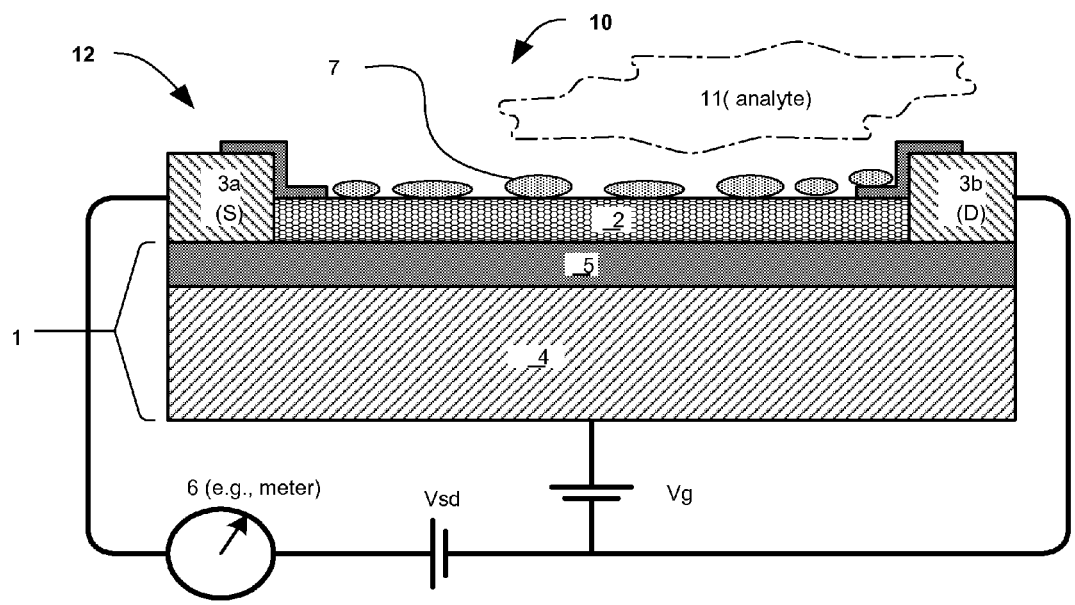
FIG. 2A

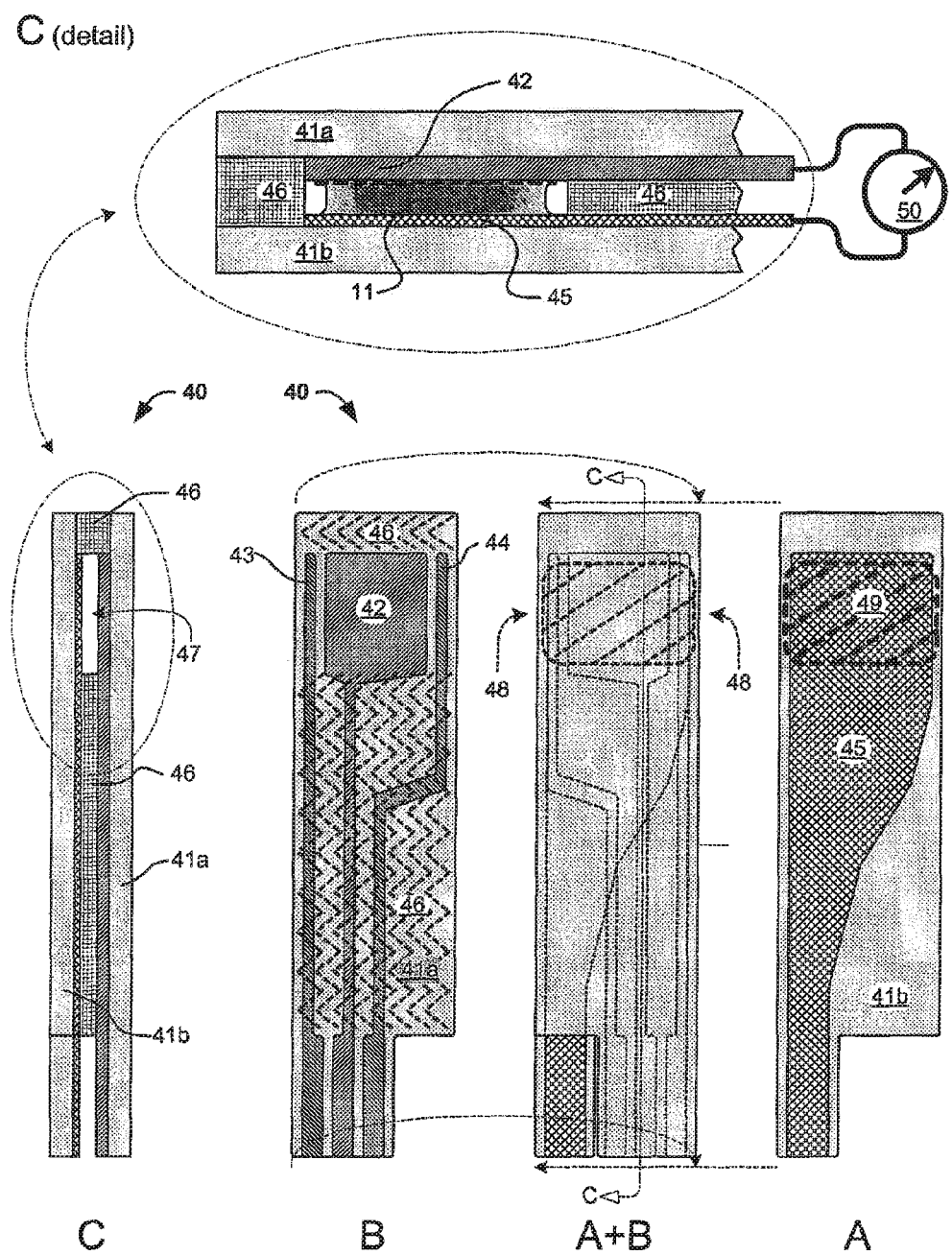
Fig. 10 (views A - C)

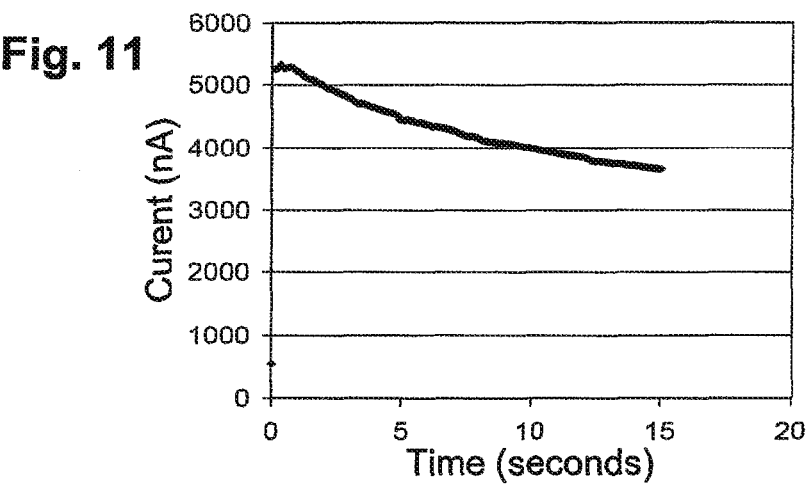
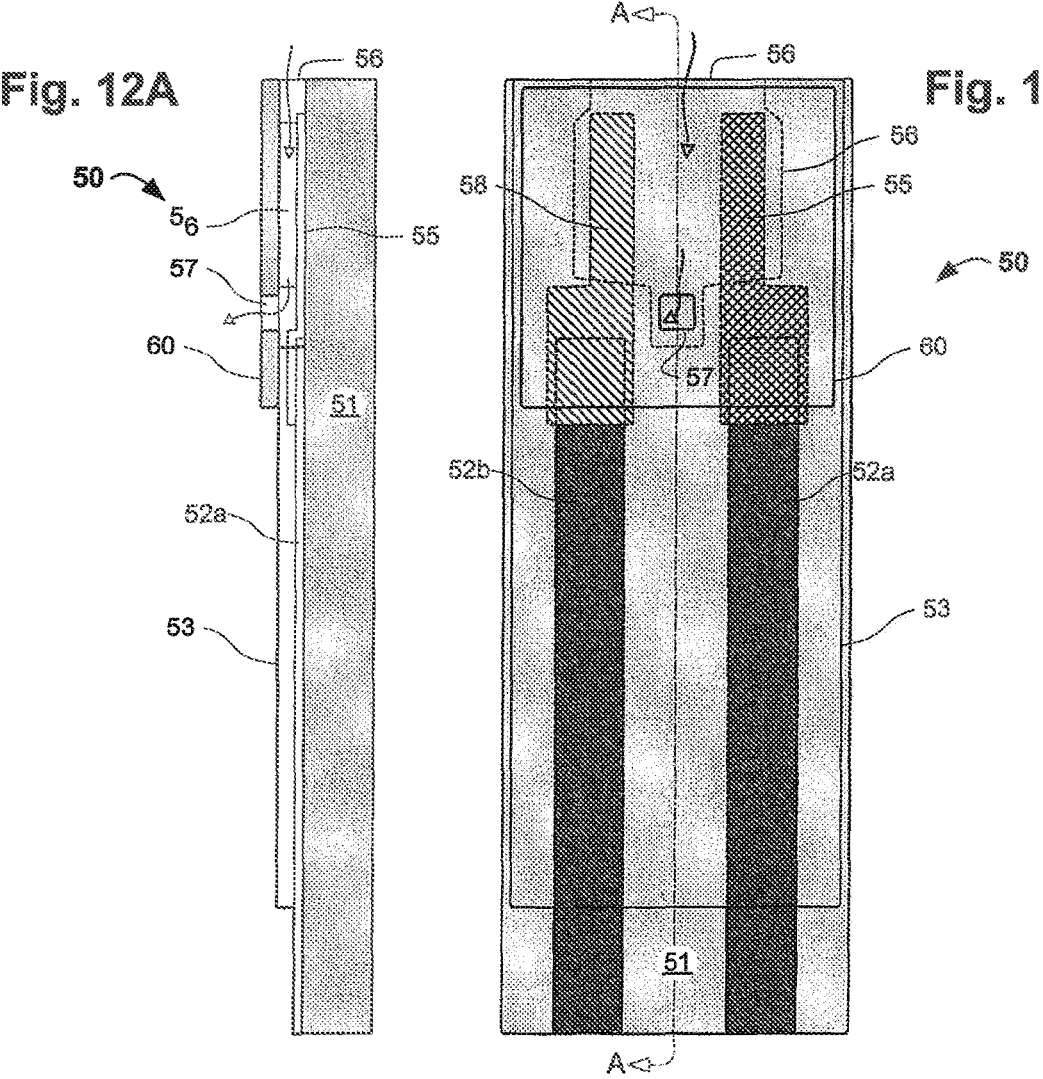

NANOELECTRONIC ELECTROCHEMICAL TEST DEVICE

CROSS REFERENCE TO RELATED APPLICATIONS

This application claims the benefit pursuant to 35 USC. §119(e) of the following US Provisional Application, which is incorporated by reference in its entirety:

US Application No. 60/937,256 filed Jun. 26, 2007, entitled "Nanoelectronic Chemical Test Device."

This application claims priority pursuant to 35 USC. §120 of the following US Application:

U.S. application Ser. No. 11/274,747 filed Nov. 15, 2005 (published US 2007-0208243-A1) entitled "Nanoelectronic Glucose Sensors," all of which is incorporated by reference in its entirety.

Each of the following commonly-assigned patent applications is incorporated by this reference in its entirety for all purposes:

U.S. Provisional Application No. 60/922,642 filed Apr. 10, 2007, entitled "Ammonia Nanosensors, Environmental Control System and Measurement Method."

U.S. Provisional Applications No. 60/850,217 filed Oct. 6, 2006, and No. 60/901,538 flied Feb. 14, 2007, each entitled "Electrochemical nanosensors for biomolecule detection."

U.S. application Ser. No. 11/636,360 filed Dec. 8, 2006, entitled "Ammonia Nanosensors, and Environmental Control System," which claims priority of U.S. No. 60/748,834, filed Dec. 9, 2005.

U.S. application Ser. No. 10/846,072 filed May 14, 2004, entitled "Flexible nanotube transistors" (published US 2005-0184,641), which claims priority to U.S. No. 60/471,243 filed May 16, 2003;

U.S. application Ser. No. 10/656,898 filed Sep. 5, 2003 entitled "Polymer Recognition Layers For Nanostructure Sensor Devices" (published US 2005-0279987), which claims priority to U.S. No. 60/408,547 filed Sep. 5, 2002;

U.S. application Ser. No. 10/945,803 filed Sep. 20, 2004 entitled "Multiple nanoparticles electrodeposited on nanostructures" (published 2005-0157,445), which claims priority to U.S. No. 60/504,663 filed Sep. 18, 2003;

U.S. application Ser. No. 10/345,783 filed Jan. 16, 2003, entitled "Electronic sensing of biological and chemical agents using functionalized nanostructure" (published US 2003-0134433), which claims priority to U.S. No. 60/349,670 filed Jan. 16, 2002; U.S. application Ser. No. 10/280,265 flied Oct. 26, 2002 entitled "Sensitivity control for nanotube sensors" (U.S. Pat. No. 6,894,159), which claims priority to U.S. No. 60/408,412 filed Sep. 4, 2002;

U.S. application Ser. No. 10/177,929 filed Jun. 21, 2002 entitled "Dispersed Growth Of Nanotubes On A Substrate."

U.S. patent application Ser. No. 11/063,504 filed Feb. 23, 2005 (published 20050186,333) entitled "Strip Electrode With Conductive Nano Tube Printing," which claims priority to U.S. No. 60/546,762 filed Feb. 23, 2004.

PCT patent application No. PCTIUS2005/019,311 filed May 31, 2005 (published W02005-119,772), entitled "Coatings comprising Carbon nanotubes" which claims priority to U.S. No. 60/576,195 filed Jun. 2, 2004.

U.S. patent application Ser. No. 11/502,811, entitled "Non-printed small volume in vitro analyze sensor and methods" filed Aug. 10, 2006 (published 2007-0037,057), which claims priority to U.S. No. 60/707,863 filed Aug. 12, 2005.

All of the foregoing patent applications identified above, together with any and all priority documents there of are specifically incorporated herein, in their entirety, by reference.

BACKGROUND OF THE INVENTION

1. Field of the Invention

The present invention relates to sensors for chemical species using nanostructured electronic devices, and methods relating to their use and manufacture, and in particular, to devices employing nanotubes as electronic transducers for the detection and measurement of solvated biomolecules or physiologic species, such as blood glucose.

2. Description of Related Art

A significant percentage of the US population suffers from diabetes (18.2 million or 6.3%). Of the 18.2 million, 13 million have been diagnosed and of the diagnosed fraction 4 million people take insulin daily. This patient group is supported through numerous foundations and professional associations who provide patient care and education.

Sources report the market growth at 15% annually, driven mainly by increased incidence of disease (obesity, diet) and increased daily monitoring by present patients. Insulin is taken to regulate blood glucose level. The amount of insulin taken must be titrated based on food intake, exercise, physical condition of the user plus the current level of glucose. For the 4 million who follow the insulin dosing protocol blood glucose measurements are suggested 4 to 6 times per day. Diabetics who are not insulin dependent check their blood glucose less frequently, typically 1 or two times a day, to adjust oral medications as well as exercise and food intake. It is estimated that this results in about 9-10 billion glucose determinations per year worldwide.

Self-measurement of glucose is common. Measuring one's own glucose level is typically called Self Monitoring of Blood Glucose (SMBG). Most 5MBG readings are done on a sample of capillary blood obtained by a finger prick. The blood is applied to a disposable sensor "strip" typically an electrochemical sensor containing Glucose Oxidase (GOX). The sensor current or voltage is read by a small electrometer referred to as a glucose meter.

An example of a popular glucose meter is shown in FIG. 1A. The strips are contained in a cartridge. The meter automatically pushes the strips out to collect blood. After use the user must manually remove each strip and dispose of it. Most glucose meters are battery driven and have a measurement range of 20-600 mg/dL. Required blood volume varies between 0.3 and 1 uL. Most meters are provided freely to get payback on strip usage. Disposable strips contain the actual glucose sensor. Capillary action is used to move the blood into the area of the sensor.

FIG. 1B shows a wearable glucose sensor. However, there is a need for glucose measurement and monitoring technology which is more convenient, cheaper, and better suited to integration into other systems, such as invasive or implantable diagnostic or therapeutic devices.

SUMMARY OF THE INVENTION

It should be understood that one aspect of the invention herein may be set forth in one part of the description, figures, formulas, and/or examples herein, while other aspects of the invention may be set forth in other parts of the description, figures, formulas, and/or examples herein. Certain advantageous inventive combinations' may be taught in one part of the description, figures, formulas, and/or examples herein, and the detailed description, and the best mode of such combinations and their respective elements may be set forth in other parts of the description, figures, formulas, and/or examples herein. Therefore the invention is to be understood broadly from this disclosure as read in its entirety, including the patent applications incorporated by reference, and including the informal claims set forth below.

Certain exemplary embodiments having aspects of the invention comprise an electronic sensor device configured for wearable monitor, which provides the convenience of longer term monitoring (e.g., 1 week), optionally with a disposable sensor element which provides cost effective benefits to patients. See U.S. application Ser. No. 11/274,747 filed Nov. 14, 2006 entitled "Nanoelectronic Glucose Sensors", which is incorporated by reference.

In certain embodiments, it is advantageous to make each sensor a single-use device, the sensor being integrated into a reusable measurement system. Alternative embodiments may include an array with multiple sensor elements on a chip, wherein the multiple sensors are configured to be used sequentially by the patient or care provider, so that the device can provide a plurality of measurements. These embodiments are arranged to take advantage of the photolithographic manufacturing technology common in the electronics industry to reduce the cost-per-measurement to a low level. Known microprocessors, output devices, displays and/or power sources and the like may be included in the sensor system. See U.S. application Ser. No. 11/274,747 filed Nov. 14, 2006 (published US) entitled "Nanoelectronic Glucose Sensors", which is incorporated by reference.

Additional exemplary embodiments having aspects of the invention comprise an electronic sensor device which is biocompatible and configured to be operated with all or a portion of the device emplaced or inserted within a patient's body. Known biocompatible materials maybe readily used to construct the sensor device. See U.S. application Ser. No. 11/274, 747 filed Nov. 14, 2006 (published US) entitled "Nanoelectronic Glucose Sensors", which is incorporated by reference.

In certain embodiments, one or more sensor devices are integrated into or coupled to a drug delivery system, such as an implantable insulin delivery device. The electronic sensor device is configured so as to control the release of one or more drugs in relation to the measured blood concentration of one or more target species, such as the controlled release of insulin relative to monitored blood glucose level. See U.S. application Ser. No. 11/274,747 filed Nov. 14, 2006 (published US) entitled "Nanoelectronic Glucose Sensors", which is incorporated by reference.

Certain embodiments of a nanoelectronic patient medical monitor system having aspects of the invention comprise: (a) an electronic control processor disposed in a patient-portable housing; (b) an analyte fluid sampling device, comprising at least one micro-needle disposed in the patient-portable housing, and configured to draw a sample of body fluid; (c) a plurality of nanosensors disposed in the a patient-portable housing and in fluid communication with the analyte fluid sampling device; configured to transmit at least one signal in response to a target analyte; (d) electrical measurement circuitry disposed in a patient-portable housing in communication with the electronic control processor; (e) a plurality of electronically actuated valves disposed in association with the analyte fluid sampling device, configured to regulate the fluid communication of the analyte fluid sampling device with a respective nanosensor; (f) the electronic control processor further including a memory and code instructions configured to selectably actuate one or more of the electronically actuated valves, and to cause the electrical measurement circuitry to detect a concentration of the target analyte using the at least one signal from the respective nanosensor. (g) Optionally, the nanoelectronic patient medical monitor system may further comprise an electronically controllable drug delivery system in communication with the electronic control processor, configured to deliver a selected dosage of a medication in response to the detect of a target analyte in the body fluid sample. See U.S. application Ser. No. 11/274,747 filed Nov. 14, 2006 (published US) entitled "Nanoelectronic Glucose Sensors", which is incorporated by reference.

Additional exemplary embodiments having aspects of the invention comprise an insulating substrate such as a polymeric base film or strip, further comprising printed or deposited conductive material configured as at least one electrode region on or adjacent the substrate surface, and further comprising a coating in communication with at least a portion of the electrode regions, the coating including at least a functionalized nanostructure such as a film of carbon nanotubes functionalized with a metal and/or an organic material. The functionalization may include a bio-selective material such as a glucose-reactive enzyme.

Certain sensor device embodiments having aspects of the invention comprise a substrate having a conductive layer, the conductive layer comprising a plurality of nanostructures (e.g., SWNTs, MWNTs, nanowires and other nanoparticles of various compositions), and preferably a network or film of single-walled carbon nanotubes. The conductive layer preferably has functionalization material or reacted groups, which may include a quantity of platinum (Pt) nanoparticles, preferably deposited on or bound to the nanostructures, such as SWNTs. In a preferred embodiment, Pt nanoparticles are produced and bound to SWNTs in solution or dispersion phase by reduction of a soluble Pt compound in a suitable solvent, the Pt functionalized SWNTs then being printed, sprayed or otherwise deposited on the substrate to form the conductive layer. Preferably a detection enzyme, such as glucose oxidase (GOx) is dispose on or in association with the conductive layer. Sensor device may includes a counter electrode disposed adjacent the conductive layer in a spaced-apart fashion, such as on a second substrate arranged adjacent the first substrate, the space between the counter electrode and conductive layer forming a sample cell for an analyte medium, for example, blood (suitable containing elements may be included to immobilize the analyte medium during sensor operation). Both counter electrode and conductive layer may be connected to suitable measurement circuitry to a change in an electrical property of the sensor in response to the presence of a target analyte. For example, glucose in a blood sample may react with GOx to form reaction products, such as hydrogen peroxide ($H_2O_2$) and gluconic acid), which in turn electrochemically generate a current flow between counter electrode and the conductive layer, which can be measured as an indication of glucose concentration.

Certain alternative sensor device embodiments having aspects of the invention comprising a conductive layer having nanostructures functionalized by binding to a conductive polymeric material, for example a polyaniline derivative such as poly (maminobenzene sulfonic acid) or PABS. This composite material may be employed with or without Pt nanoparticles. Certain alternative sensor architectures may be employed in association with a conductive layer comprising a nanostructure/conductive polymer composite (such as SWNT/PABS) for detection of analytes, without departing from the spirit of the inventions. For example the sensor may be configured as a resistance sensor, an FET, a capacitance or impedance sensor, or the like, and may be arranged as an array including a combination of these.

Additional embodiments of the invention relate to methods of fabricating nanoelectronic sensors that involve single step deposition of the carbon nanotubes and functional biomolecules (having a functionalization that allows interact with the analyte) on the sensor surface. The biomolecule and carbon nanotubes interact prior to deposition, enabling single step deposition. The biomolecule (e.g., an enzyme, mediator, nucleic acid, antibody, etc.) retains its activity and stability after immobilization on the electrode.

Additional aspects and embodiments of the invention are set forth in the various Examples in the Figures and in the Detailed Description Of The Embodiments

BRIEF DESCRIPTION OF DRAWINGS

The figures and drawings may be summarized as follows:
FIG. 1A shows an existing glucose sensor:
FIG. 1B shows an existing wearable glucose sensor;
FIG. 2A is a schematic cross section view of a nanostructure device having aspects of the invention with a recognition layer specific to a selected analyte.
FIGS. 4A-4C illustrate alternative embodiments of sensors having solution deposited nanotube networks, wherein:
FIG. 4A shows a sensor in which a recognition layer is applied following deposition of nanotube film;
FIG. 4B shows a sensor in which a layer of recognition material is deposited upon the substrate prior to application of a nanotube film 2;
and
FIG. 4C shows a sensor which includes a layer of pre-functionalized nanotubes without a distinct recognition layer.
FIG. 7 shows architecture of a sensor device embodiment having aspects of the invention for detection and measurement of biomolecular species such as polynucleotides, proteins, polysaccharides and the like.
FIG. 10 (Views A-C) illustrate an exemplary electrochemical sensor configured as a blood test strip.
FIG. 11 is a plot showing the response of a electrochemical sensor embodiment functionalized with SWNT-PABS.
FIGS. 12A-12B illustrate an exemplary electrochemical test strip having a CNT working electrode and a vented capillary path.

DETAILED DESCRIPTION OF PREFERRED EMBODIMENTS

Figure 2B:
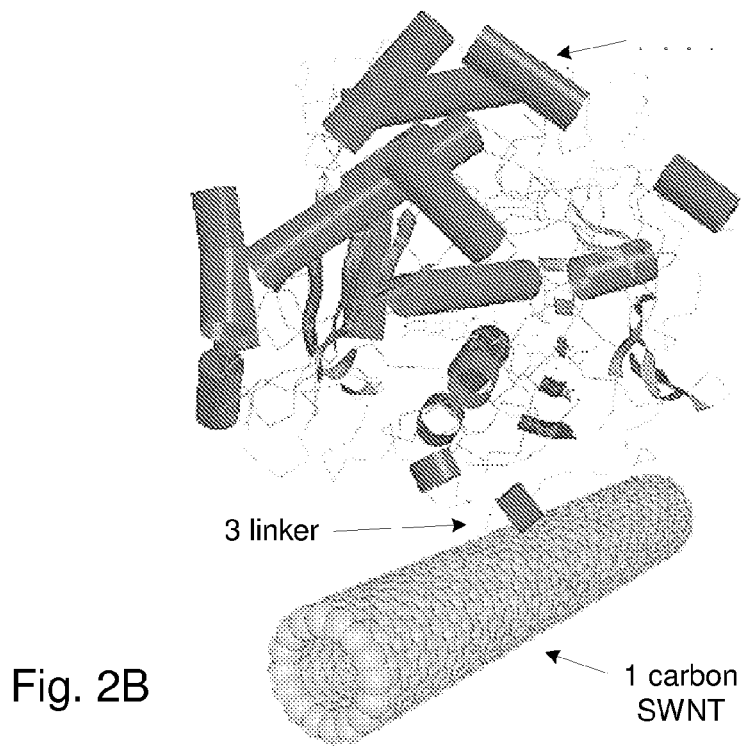
FIG. 2B is a schematic diagram of GOx functionalization of a nanotube sensor embodiment.

The making, functionalization and use of nanostructured chemosensor and biosensor devices is described in considerable detail in the patent applications incorporated by reference above.

Example A

NTFET Glucose Sensor

A number of preferred sensor embodiments employ nanostructures, such as nanotubes. FIG. 2A. shows an electronic sensing device 10 for detecting a liquid or gaseous analyte 11, comprising a nanostructure sensor 12. Device 12 comprises a substrate 1, and a conducting channel or layer 2 including nanostructured material disposed upon a substrate 1.

The nanostructured material may contact the substrate as shown, or in the alternative, may be spaced a distance away from the substrate, with or without a layer of intervening material. As used herein, a "nanostructured material" includes any object or objects which has at least one dimension smaller than about 100 nm and comprises at least one sheet of crystalline material with graphite-like chemical bands. Examples include, but are not limited to, single-walled nanotubes, double-walled nanotubes, multi-walled nanotubes, and "nanoanions." Chemical constituents of the crystalline material include, but are not limited to, carbon, boron nitride, molybdenum disulfide, and tungsten disulfide. Preferably a nanotube is a carbon nanotube, and more preferably it is a single-walled carbon nanotube.

In an embodiment of the invention, conducting channel 2 may comprise one or more carbon nanotubes. For example, conducting channel 2 may comprise a plurality of nanotubes forming an interconnecting mesh, film or network Typically, a "nanotube network" is a film of nanotubes disposed on a substrate in a defined area A film of nanotubes comprises at least one nanotube disposed on a substrate in such a way that the nanotube is substantially parallel to the substrate. The film may comprise many nanotubes oriented generally parallel to each other. Alternatively, the film may comprise many nanotubes, each oriented substantially randomly with respect to adjacent nanotubes, or the nanotubes may be oriented substantially perpendicular to the substrate, e.g., as in a "nanoturf" configuration.

The number of nanotubes in as area of substrate is referred to as the density of a network. Preferably, the film comprises many nanotubes oriented substantially randomly, with the density high enough that electric current may pass through the network from one side of the defined area to the other side. Methods for disposing a high density of nanotubes are disclosed in U.S. application Ser. No. 10/177,929, filed Jun. 21, 2002 by Gabriel et al. (equivalent to W02004-040,671), which is incorporated by reference.

Solvent/suspension Deposition Nanoparticle Network. Alternatively, a nanotube network may be deposited on a device substrate by spray deposition and the like. Such methods as spin coating, spray deposition, dip coating and ink jet printing may be employed to deposit the solution or suspension of nanostructures, such as nanotubes.

For example, single wall carbon nanotubes (SWNTs) and/or other nanoparticles may be suspended in a suitable fluid solvent, and sprayed, printed or otherwise deposited in a substrate. The SWNTs or other nanoparticles may optionally have additional functionalization groups, purification and/or other pre-deposition processing. For example SWNTs functionalized with poly m-aminobenzene sulfonic acid (PABS) show hydrophilic properties and may be dispersed in aqueous solutions.

One or more conductive traces or electrodes may be deposited after deposition, or alternatively, the substrate may include pre-patterned electrodes or traces exposed • on the substrate surface. Similarly, alternative embodiments may have a gate electrode and a source electrode supported on a single substrate. The substrate may include a flat, sheet-like portion, although one skilled in the art will appreciate that geometric variations of substrate configurations (rods, tubes or the like) may be employed without departing from the spirit of the inventions.

The density of a network of nanotubes (or other nanostructure elements) maybe adjusted to achieve a selected conductivity in an electrically continuous network via interconnections between adjacent nanotubes (e.g., a CNT film of density close to but greater than the percolation limit). For example, this may be achieved through controlled CVD conditions, e.g., catalyst particle density, deposition environment, duration, or the like (see Ser. No. 10/177,929, filed Jun. 21, 2002).

In another example, density of a network of nanotubes may be controlled by flow through a filter membrane. In such embodiments, a micro-porous filter, membrane or substrate may be employed in deposition of a nanotube (or other nanoparticle) network channel from suspension or solution. A porous substrate can accelerate deposition by removing solvent so as to minimize "clumping", anal can assist in controlling deposition density. The deposition may be carved out by capillary absorption, or using suction or vacuum deposition across the porous substrate or membrane, as described in the above referenced application Ser. No. 10/846,072 (e.g., see description of FIG. 3 and Example B of that application); in U.S. Provisional Application No. 60/639,954 filed Dec. 28, 2004 entitled 'Nanotube Network On-Top Architecture For Biosensor'; and in L. Hu et al., Percolation in Transparent and Conducting Carbon Nanotube Networks, Nano Letters (2004), 4, 12, 2513-17, each of which application and publication is incorporated herein by reference. The network thus formed may be separated from the deposition membrane using a method such as membrane dissolution or transfer bonding, and included in a sensor device structure as a conducting channel (e.g., disposed on a device substrate, contact grid, or the like).

In a spray-deposition example, multiple light, uniform spray steps may be performed (e.g., with drying and resistance testing between spray steps) until the network sheet resistance reaches a target value (implying a target network density and conductivity). In one example, P2-SWNTs produced by Carbon Solutions, Inc of Riverside, Calif. were spray-deposited on a portion of a PET sheet substrate with pre-patterned traces until a sheet resistance about 1 kS1 was reached.

Dispersed networks of nanotubes and methods of formation are further described in U.S. application Ser. No. 11/636, 360 filed Dec. 8, 2006 (published US), U.S. application Ser. No. 11/274,747 filed Nov. 14, 2006 (published US); and U.S. application Ser. No. 10/846,072 filed May 14, 2004 (published US 2005-0184,641), each of which is incorporated by reference.

Substrates may be flat objects that are electrically insulating. Substrates have a chemical composition, of which examples include, but are not limited to, silicon oxide, silicon nitride, aluminum bride, polyimide, and polycarbonate. Preferably the substrate is a silicon oxide film on a silicon chip.

One or more conductive elements or contacts $3a$, $3b$ may be disposed over the substrate and electrically connected to conducting channel $2$. Elements $3a$, $3b$ may comprise metal electrodes in direct contact with conducting channel $2$. In the alternative, a conductive or semi-conducting material (not shown) may be interposed between contacts $3$; $3b$ and conducting channel $2$. Contacts $3a$, $3b$ may comprise a source electrode S and a drain electrode D upon application of a selected and/or controllable source-drain voltage Vsd (note that the voltage and/or polarity of source relative to drain may be variable, e.g., current may be DC, AC and/or pulsed, and the like). In such case, the contacts are arranged so that the nanotube network comprises at least one conductive path between at least a pair of conductors.

Alternatively, a contact or electrode may be employed to provide a charge to the channel $2$ relative to a second electrode, such that there is an electrical capacitance between the second electrode and the channel $2$. The second electrode may be a gate electrode, a discrete bottom electrode (e.g. embedded in, under, and/or doped within the substrate), a top gate electrode, a liquid medium electrode, and the like. In another exemplary preferred embodiment, the gate electrode is a conducting element in contact with a conducting liquid, said liquid being in contact with the nanotube network. In other embodiments, the device includes a counter electrode, reference electrode and/or pseudo-reference electrode.

In one exemplary preferred embodiment, the gate electrode is a conducting plane within the substrate beneath the silicon oxide. Examples of such nanotube electronic devices are provided, among other places, in application Ser. Nos. 10/656,898, filed Sep. 5, 2003 (US 2005-0279987) and 10/704,066, filed Nov. 7, 2003 (US 2004-0132,070), both of which are incorporated by reference. FIG. 2A, the device $10$ may operate as a gate-controlled field effect transistor via the effect of gate electrode $4$. In this example, the gate $4$ comprises a base portion of the substrate, such as doped-silicon wafer material isolated from contacts $3a$, $3b$ and channel $2$ by dielectric $5$, so as to permit a capacitance to be created by an applied gate voltage Vg. For example, the substrate $1$ may comprise a silicon back gate $4$, isolated by a dielectric layer $5$ of SiO2. Such devices are generally referred to herein as nanotube field effect transistors (NTFET).

Embodiments of an electronic sensor device having aspects of the invention may include an electrical circuit configured to measure one or more properties of the nanotube sensor, such as measuring an electrical property via the conducting elements. For example, a conventional power source may supply a source drain voltage Vsd between contacts $3a$, $3b$. Measurements via the sensor device $10$ may be carried out by circuitry represented schematically by meter $6$ connected between contacts $3a$, $3b$. In embodiments including a gate electrode $4$, a conventional power source may be connected to provide a selected and/or controllable gate voltage Vg. Device 10 may include one or more electrical supplies and/or a signal control and processing unit (not shown) as known in the art, in communication with the sensor 12.

Any suitable electrical property may provide the basis for sensor sensitivity, for example, electrical resistance, electrical conductance, current, voltage, capacitance, transistor on current, transistor off current, and/or transistor threshold voltage. Alternatively, sensitivity may be based on measurements including a combination, relationship, pattern and/or ratios of properties and/or the variation of one or more properties over time. For example, the capacitance or impedance of the nanostructures relative to a gate or counter electrode. Similarly, a breakdown voltage or electron emission voltage and/or current may be measured between nanostructures and a reference electrode.

In certain embodiments, a transistor sensor may be controllably scanned through a selected range of gate voltages, the voltages compared to corresponding measured sensor current flow (generally referred to herein as an I-Vg curve or scan). Such an I-Vg scan may be through any selected gate voltage range and at one or more selected source-drain potentials. The Vg range is typically selected from at least device "on" voltage through at least the device "off" voltage. The scan can be either with increasing Vg, decreasing Vg, or both, and may be cycled +− at any selected frequency.

From such measurements, and from derived properties such as hysteresis, time constants, phase shifts, and/or scan rate/frequency dependence, and the like, correlations may be determined with target detection and/or concentration and the like. The electronic sensor device may include and/or be coupled with a suitable microprocessor or other computer device of known design, which may be suitably programmed to carry out the measurement methods and analyze the resultant signals. Those skilled in the art will appreciate that other electrical and/or magnetic properties, and the like may also be measured as a basis for sensitivity. Accordingly, this list is not meant to be restrictive of the types of device properties that can be measured.

In certain embodiments, sensor 12 may further comprise a layer of inhibiting or passivation material 6 covering regions adjacent to the connections between the conductive elements 3a, 3b and conducting channel 2. The inhibiting material may be impermeable to at least one chemical species, such as the analyte 11. The inhibiting material may comprise a passivation material as known in the art, such as silicon dioxide, aluminum oxide, silicon nitride, and the like. Further details concerning the use of inhibiting materials in a NTFET are described in prior application Ser. No. 10/280,265, filed Oct. 26, 2002 (US 2004-0043527), which is incorporated by reference herein.

The conducting channel 2 (e.g., a carbon nanotube layer) is typically functionalized to produce a sensitivity to one or more target analytes 11. Although nanoparticles such as carbon nanotubes may respond to a target analyze through charge transfer or other interaction between the device and the analyte, more generally a specific sensitivity can be achieved by employing recognition material 7 that induces a measurable change the device characteristics upon interaction with a target analyze. Typically, the sensor functionalization layer 7 is selected for a specific application. The analyte may produce the measurable change by electron transfer, and/or may influence local environment properties, such as pH and the like, so as to indirectly change device characteristics. Alternatively or additionally, the recognition material may induce electrically-measurable mechanical stresses or shape changes in the conducting channel 2 upon interaction with a target analyte.

In a typical embodiment having aspects of the invention, the sensitivity is produced and/or regulated by the association of the nanotube layer 2 with a functionalization material, e.g. disposed as a functionalization layer 7 adjacent channel 2. The functionalization layer 7 may be of a composition selected to provide a desired sensitivity to one or more target species or analytes. The functionalization material may be disposed on one or more discrete portions of the device, such as on all or a portion of the channel 2, or alternatively may be dispersed over the sensor 12, such as on contacts 3 and/or exposed substrate 1.

Optionally device 10 may comprise a plurality of sensors 12 disposed in a pattern or affray, as described in U.S. patent application Ser. No. 10/388,701 filed Mar. 14, 2003 entitled "Modification Of Selectivity For Sensing For Nanostructure Device Arrays" (now published as US 2003-0175161). Each device in the array can be functionalized with identical or different functionalization. Identical device in an array can be useful in order to multiplex the measurement to improve the signal/noise ratio or increase the robustness of the device by making redundancy.

The above described sensor embodiments, such as a preferred embodiment of a carbon nanotube network transistor, may be treated or engaged with many alternative functionalization materials, probes, molecular transducers, coatings and the like.

In one example of a glucose sensor, the network is functionalized using the enzyme glucose oxidase (GOx), so as to provide glucose-specific sensitivity. FIG. 2B diagrammatically illustrates the functionalization. In one preferred example, the GOx (or an alternative biomolecule probe) may be bonded to a linker molecule, such as pyrene, polymer or the like. (See patent application Ser. No. 10/345,783 incorporated by reference above).

The linker molecule, in turn, is selected to have properties which cause it to associate with the lattice of the carbon nanotube, such as by non-covalent pi-pi stacking between the graphitic nanotube lattice and the flat ring pyrene structure. (see Besteman, et al., *Enzyme Coated Carbon Nanotubes As Single Molecule Biosensors*, Nano Letters, 2003 Vol. 3, No. 6, 727-730) Such a functionalization structure is referred to as a molecular transducer.

Figure 3:
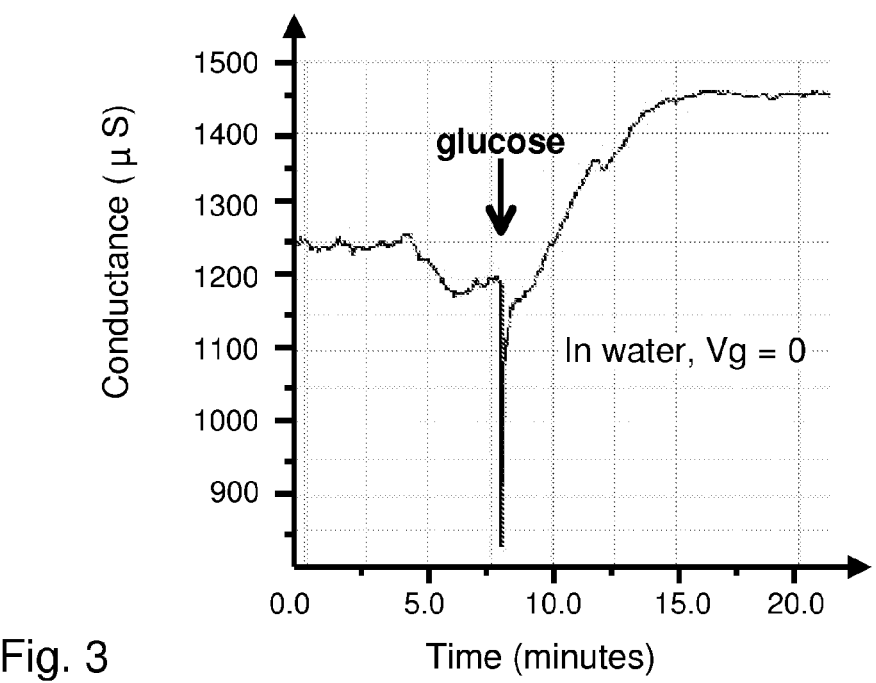
FIG. 3 is a plot showing the response of a sensor embodiment to glucose in water.

In operation of the sensor, the immobilized GOx reacts with glucose presented in the contacting medium so as to alter the electrical properties of the nanotube device. FIG. 3 shows a plot of the response of a NT sensor device (in this example the device is a NTFET generally as shown in FIG. 2A) with Vgate=0). Initially, in a water medium without glucose, the conductance is about 1200-1250 muS. Upon injection of a glucose sample (at arrow) the conductance rises to a stable level of about 1450 muS. There is an very brief transient at injection, which is believed to be an artifact of the injection process (brief exposure to air). The change in conductance may be correlated with the concentration of glucose. The response time and transient may be controlled by appropriate sample presentation, such as by rapid mixing to equilibrium concentration in contact with functionalized nanotube network. The response of the NT sensor toward an increased conductance is indicative of the effect of the biochemical environment (GOx reacting with aqueous glucose solution) on the conductance of the nanotube network channel 2 as measured between source 3a and drain 3b.

Alternative enzymes may be employed for chemodetection and biodetection in a manner similar to that described above. For example, an alternative glucose sensor system embodiment is functionalized using the enzyme methane reductase, so as to provide sensitivity to methane for methane measurement and detection. In addition other reactive or receptive biomolecules can target particular species, such as direct or indirect antibody reactions. For example, the probe may be a commercially available anti-HIV antibody which is reactive to target components of the HIV virus in a patient sample. Alternatively the probe may be a commercially available HIV antigen component, reactive to target human anti-HIV antibodies (from patient sample).

One of ordinary skill in the art can readily identify useful known probe-target combinations of biomolecules, such as enzymes and their substrates, antibodies and their specific antigens, and the like, which may be used to produce the molecular transducers for alternative embodiments, without departing from the spirit of the invention and without undue experimentation. Note that the sensor arrays described above may be included in system embodiments sensitive to multiple targets. Alternatively, the arrays may providing multiple differently functionalized sensors for the same target species, to enhance selectivity, sensitivity, dynamic range, and the like.

Example B

Sensor with Solution Deposited Nanotube Network

Figure 4A:
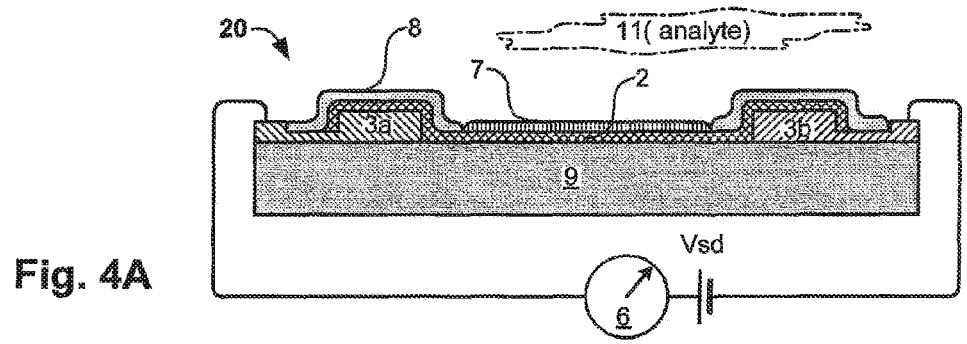

FIG. 4A is a diagram of an alternative exemplary embodiment of a nanosensor 20 having aspects to the invention, including a network of carbon nanotubes. Certain elements are generally similar to those of FIG. 2A, and the same reference numbers are indicated.

Sensor 20 comprises a substrate 9, which preferably comprises a flexible sheet-like material such a polyester polymer (e.g., PET sheet). One or more electrodes (3a and 3b are shown) are arranged on the substrate. The electrode may comprise a metal, or may be' formed from a paste or ink-like composition, such as carbon, graphite, conductive polymer, metallic ink compositions, and the like.

A nanostructure layer 2 (in this example a film including SWNTs) is deposited contacting the electrodes 3a (and 3b in this example). An optional functionalization or recognition layer 7 may be included in association with the layer 2, for example applied following deposition of SWNT film 2. An optional passivation, protective or inhibiting layer 8 may cover electrodes 3 and all or a portion of layers 2 and 7.

In a preferred embodiment, substrate 9 is a flexible sheet having pre-pattered printed electrodes 3, permitting simplicity and cost reduction. Preferably the nanostructure layer 2 is formed by spraying or otherwise coating the patterned substrate with an liquid suspension of nanotubes. For example, SWNTs or MWNTs may be conveniently dispersed in aqueous suspension at a desired concentration, particularly where functionalization treatment of the SWNTs assist in making the nanotubes hydrophilic (see EXAMPLES D-F below). Alternatively organic solvents may likewise be used to disperse and apply the nanotube film 2. See U.S. patent Ser. No. 10/846,072; and L. Hu et al., Percolation in Transparent and conducting Carbon Nanotube Networks, Nano Letters (2004), 4, 12, 2513-17, each of which is incorporated herein by reference.

In certain embodiments, recognition or detection material is deposited, reacted or bound to the nanotubes (or alternative nanostructures) prior to deposition of layer 2. Depending on the selected detection chemistry and analyte target, such pre-functionalization may eliminate the need for any distinct recognition layer 7.

Alternative nanotube dispersion techniques may also be employed, see for example, U.S. patent application Ser. No. 10/846,072 entitled "Flexible Nanotube Transistors"; and L. Hu et al., Percolation in Transparent and Conducting Carbon Nanotube Networks, Nano Letters (2004), 4, 12, 2513-17, each of which application and publication is incorporated herein by reference.

The nanostructure layer 2 may be deposited stepwise, with intermediate drying, to permit the density and conductivity of the layer 2 to be accurately controlled, such as by probe-testing the layer resistance or conductance between deposition steps, until a selected layer conductivity or resistance is achieved.

In the example of FIG. 4A, the electrodes 3a, 3b are shown deposited upon substrate 9 beneath the SWNT film 2, as this advantageously permits the use of substrates having pre-printed or pre-patterned electrode material, which permits substantial costs savings in volume production. However, other electrode configurations are possible without departing from the spirit of the invention.

Figure 4B:
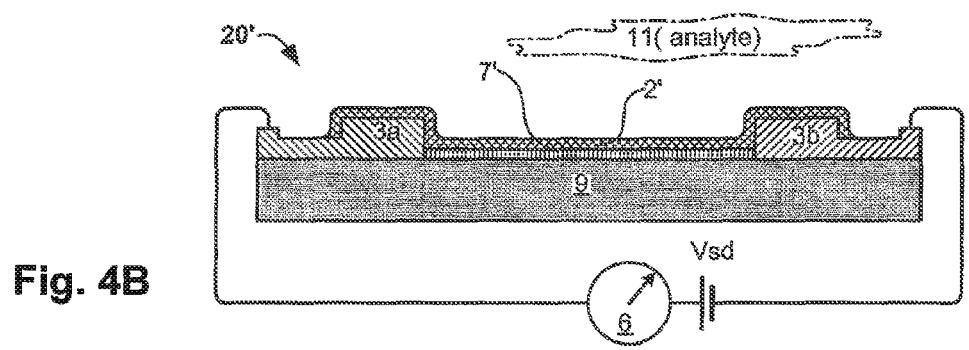

In the example shown in FIG. 4B, a layer of recognition material 7' is deposited upon the substrate or to application of the nanotube film 2, and is disposed underneath, film 2. In either of the examples of FIGS. 4A and 4B, a recognition material may penetrate the nanotube network 2 so as to be incorporated as a mixture.

Figure 4C:
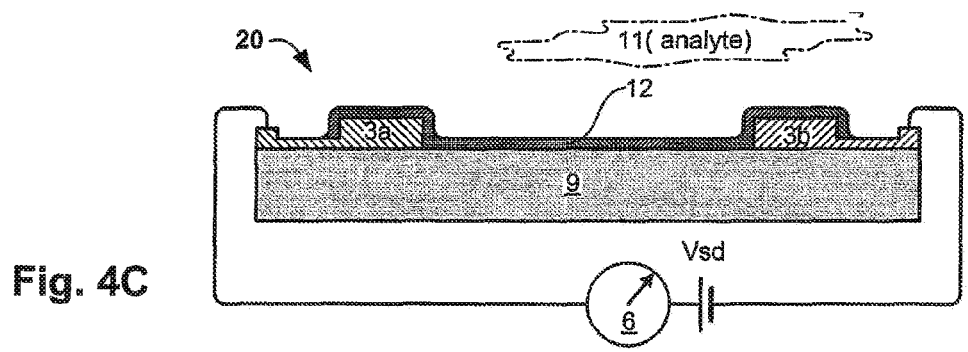

In certain embodiments, recognition or detection material is deposited, reacted or bound to the nanotubes (or alternative nanostructures) prior to deposition of layer 2. Depending on the selected detection chemistry and analyte target, such pre-functionalization may eliminate the need for any distinct recognition layer 7. In the example shown in FIG. 4C, a layer of pre-functionalized nanotubes 12 is deposited upon the substrate, without arty separate application of a recognition or functionalization material.

The nanostructure layer 2 may be deposited stepwise, with intermediate drying, to permit the density and conductivity of the layer 2 to be accurately controlled, such as by probe-testing the layer resistance or conductance between deposition steps, until a selected layer conductivity or resistance is achieved.

Suitable measurement circuitry is included in communication with electrodes 3a and 3b (and any optional additional electrodes), here represented by meter 6 and source-drain power source W.

Figure 5:
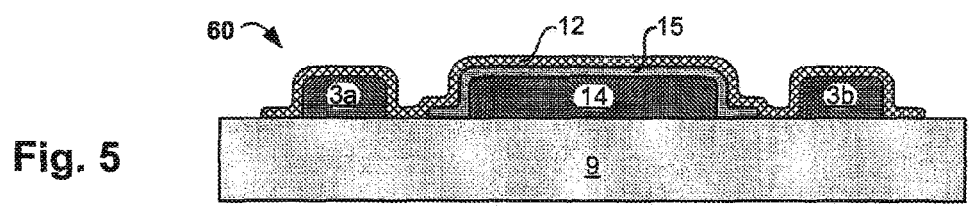
FIG. 5 illustrates an alternative embodiment of a sensor having aspects of the invention and including nanotube networks fabricated by deposition of a solution upon flexible substrates with pre-patterned conductor traces, including a gate dielectric and gate electrode.

FIG. 5 shows a NTFET alternative sensor 60 having space-apart source and drain traces 3a and 3b disposed on substrate 9. An additional intermediate trace 14 is coated with a thin layer of dielectric or insulating material 15 (organic film or inorganic deposit) prior to deposition of nanotube layer 12, so as to form a gate electrode (permitting operation as a transistor).

In one example, dielectric material 15 is a ALD layer comprising $Al_2O_3$, $ZrO_2$, or the like. Material 15 may be only a few nanometer in thickness (e.g., between about 10 and about 100 nm). Further description of ALD methods may by found in P. Chen, et al, "*Atomic Layer Deposition to Fine-Tune the Surface Properties and Diameters of Fabricated Nanopores*", Nano Lett (June 2004) Vol. 4, No. 7, pp 1333-37; D. Farmer et al, "Atomic Layer Deposition on Suspended Single-Walled Carbon Nanotubes via Gas-Phase Noncovalent Functionalization", Nano Lett (March 2006) Vol. 6, No. 4, pp 699-703; and M. Groner et al, "*Gas diffusion barriers on polymers using $Al_2O_3$ atomic layer deposition*", Appl. Phys. Lett. (2006) Vol. 88, pp 051907-1 to -3; which publications are incorporated by reference.

Example C

Sensor Having a Pre-Functionalized Nanotube Network

Figure 6:
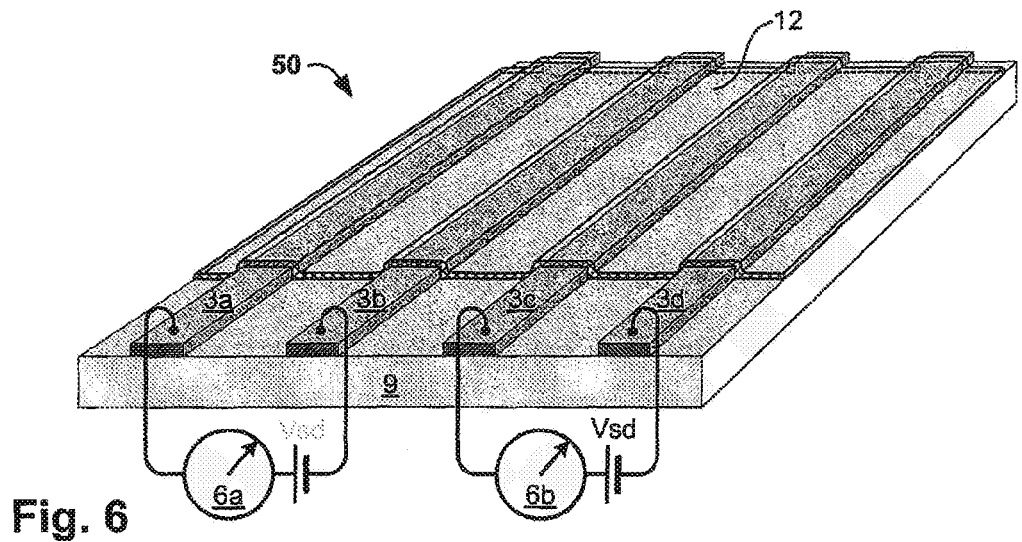
FIG. 6 shows an exemplary embodiment of a sensor device 50 having aspects of the invention and including a nanotube networks fabricated by deposition of a solution of pre-functionalized nanotubes upon a substrate.

Sensor fabrication. FIG. 6 shows an exemplary embodiment of a sensor device 50 having aspects of the invention and including a nanotube networks fabricated by deposition of a solution or dispersion of nanotubes upon a substrate 9 to form a nanotube film 12. In an exemplary embodiment shown in FIG. 6, the nanotubes (or other nanostructures) are dispersed in a volatile solvent which evaporates following deposition to leave the nanotubes configured as an open network 12.

Although electrical contacts may be deposited or applied subsequent to nanotube deposition, it is convenient and advantageous to pattern desired electrode or contact material 3 upon the substrate 9 prior to nanotube deposition (four contacts 3a-3d are shown). For example, substrates (e.g., polymer sheets such as PET, polystyrene, polycarbonate and the like) are commercially made having printable conductor material applied in a selected pattern (e.g., carbon, silver, gold, silver/silver chloride, mixtures and the like). A suitable flexible PET substrates with a pattern of printed conductive carbon traces may purchased from Conductive Technologies, Inc., of York, Pa., for example, a flexible PET substrate with screen-printed carbon paste electrodes, with spacing between the conductive traces of about 1 mm. A plurality of devices may conveniently be fabricated on a sheet of substrate material, and may subsequently be partitioned and packaged as desired, either as single sensor devices, or as arrays of sensors, and the no.

In an exemplary embodiment having aspects of the invention, the nanotube network was formed from SWNTs which were functionalized by covalently bonded poly-(m-aminobenzene sulfonic acid ("PAWS"). C'-bon nanotubes, preferably SWNTs, may be reacted and treated with PAWS (composite referred to as "ST-PAWS") by the methods as described in B Mao et al, "*Synthesis and Properties of a Water-Soluble Single-Walled Carbon Nanotube Poly-(m-aminobenzene sulfonic acid) Graft Copolymer*", Adv Funct Mater (2004) Vol 14, No 1 pp 71-76, which article is incorporated by reference. A suitable nanotube composite material ("SWNT-PABS") may be obtained from Carbon Solutions, Inc. of Riverside, Calif. in the form of a dry powder.

A variety of alternative functionalization species may be included, such as conductive polymeric materials, polyaniline (PANT), polypyrrole, polyaniline derivatives, and the alternative materials described above in TABLE 3 of U.S. application Ser. No. 11/636,360 filed Dec. 8, 2006 (published US 2008/0093226), which is incorporated by reference.

See, for example, the electrochemical treatments described in T Zhang et al, "*Nanonose: Electrochemically Functionalized Single-Walled Carbon Nanotube Gas Sensor Array*", Proc. 208th Meeting of Electrochemical Society (Los Angeles, Calif. Oct. 16-21, 2005), which is incorporated. by reference.

A suitable aqueous deposition solution may be made by suspending SWNT-PABS powder in water (preferably at a concentration of about 1 mg/mL.), and ultrasonication may be employed to assist in making a homogeneous dispersion. The carbon nanotube dispersion may be sprayed with an air brush to coat the substrate.

Preferably the deposition is done in several light coating as with intermediate drying (for example on a hotplate with the temperature of about 55 to 75 degree C.). The film resistance may be measured between steps until the selected resistance is obtained (the measurement may be between printed traces, or may be by pin probes on the network coating. For example, the deposition may be continued until resistance with a half-inch pin probe spacing is about 15 K Ohm.

Example D

CNT Electrochemical Sensor

Exemplary Sensor Devices.

Figure 7:
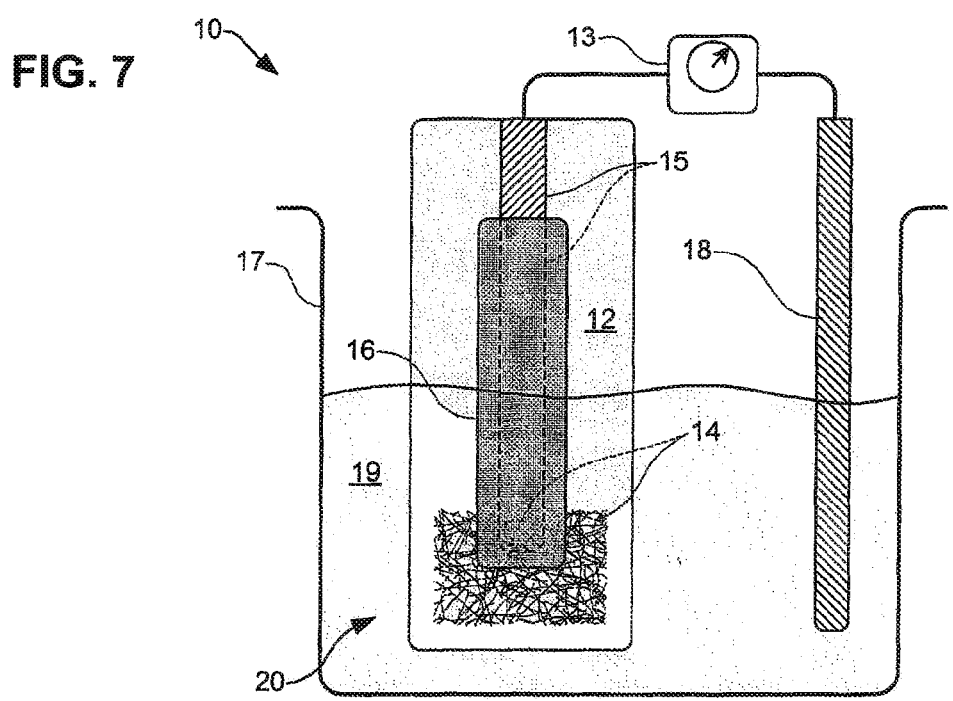

FIG. 7 shows schematic architecture of a sensor device embodiment having aspects of the invention for detection and measurement of biomolecular species, as described in further detail in U.S. Provisional Applications No. 60/850,217 filed Oct. 6, 2005, and No. 60/901,538 filed Feb. 14, 2007, each entitled "Electrochemical nanosensors for biomolecule detection", which are incorporated by reference.

In a particular example, device 10 may be employed detection of a molecular species of biological origin. The device 10 comprises a sensor substrate 12 (e.g., comprising PET, polycarbonate, flexible polymers, or the like) having a reaction or sensor tip portion of its surface 20 on which an interconnecting carbon nanotube (CNT) network 14 is disposed. In the example of FIG. 1, a conductive trace or drain 15 electrically communicates with the network 14 (e.g., silver ink may be deposited on the substrate 12 so as to contact a portion of the network 14).

Device 10 includes a well or container 17 holding buffer or fluid media 19 in which both sensor tip 20 and a gate electrode 18 are immersed. In certain embodiments, gate electrode 18 may include a reference electrode, such as a Ag/AgCl reference electrode, saturated calomel electrode, or the like. One skilled in the art will appreciate that container 17 may comprise one or more microfluidic elements, capillaries, sampling devices, incubators, and the like, without departing from the spirit of the invention.

An encapsulation material 16 (e.g., polymers such as epoxy, $Al_2O_3$, $Si_4N_3$, $SiO_2$, ALD layers, and the like) may be deposited so as to isolate portions of the device from the medium or buffer 19, while not covering at least a portion of the CNT network 14.

With reference to encapsulation material 16 and to other encapsulation layers, dielectric layers and/or isolation layers or multi-layer structures included in alternative embodiments having aspects of the invention described herein, it may be advantageous to produce layers that are extremely flan and uniform, while at the same time avoiding pores, shadowing or other discontinuities/irregularities in the coating. It may also be desirable in certain elements to avoid damage to underlying elements, such as carbon nanotube networks. Atomic layer deposition methods provide alternative approaches to producing a layer or coating having the desirable qualities, and may be employed to deposit a layer of an oxide, nitride or other compound, or combinations or multiple layers of these. Alternative methods may be used, such as thermal and e-beam evaporation. Additional process elements may be included to improve 'coating properties, such as rotating and/or tilting a substrate during evaporation. Further description of ALD methods may found in P. Chen, et al, "*Atomic Layer Deposition to Fine-Tune the Surface Properties and Diameters of Fabricated Nanopores*", Nano Lett (June 2004) Vol. 4, No. 7, pp 1333-37; D. Farmer et al, "*Atomic Layer Deposition on Suspended Single-Walled Carbon Nanotubes via Gas-Phase Noncovalent Functionalization*", Nano Lett (March 2006) Vol. 6, No. 4, pp 699-703; and M. Groner et al, "*Gas diffusion barriers on polymers using Al203 atomic layer deposition*", Appl. Phys. Lett. (2006} Vol. 88, pp 051907-1; which publications are incorporated by reference.

Drain 15 and gate 18 are connected to suitable measurement circuitry 13, which may comprise one or more of a number of devices conventionally used for signal measurement, recordation, display, power supply, signal processing and/or logic operations, and the like, as described farther herein. Additional or substitute electrodes may also be included in device 10, such as counter electrodes, reference electrodes and the like, such as Ag/AgCl reference electrodes described herein.

A CNT network may be made by methods described above with respect to EXAMPLES A-C, such as by CVD formation of CNT from catalyst nanoparticles (see Ser. No. 10/177, 929), by spray deposition, or the like.

One or more conductive traces or electrodes may be deposited after deposition, or alternatively, the substrate may include pre-patterned electrodes or traces exposed on the substrate surface. Similarly, alternative embodiments may have a gate electrode and a source electrode supported on a single substrate. The substrate may include a flat, sheet-like portion, although one skilled in the art will appreciate that geometric variations of substrate configurations (rods, tubes or the like) may be employed without departing from the spirit of the inventions.

Analyte-specific functionalization may be included on or adjacent to network 14, such as redox enzymes capable of producing an electroactive species when bound to an analyte as a substrate (e.g., glucose oxidase active on a glucose substrate). Alternative functionalization includes analyte-specific receptors or binding probes, such as antibodies, oligonucleotides, and the like.

Redox Couple Species to Enhance Electron Transfer.

Figure 8:
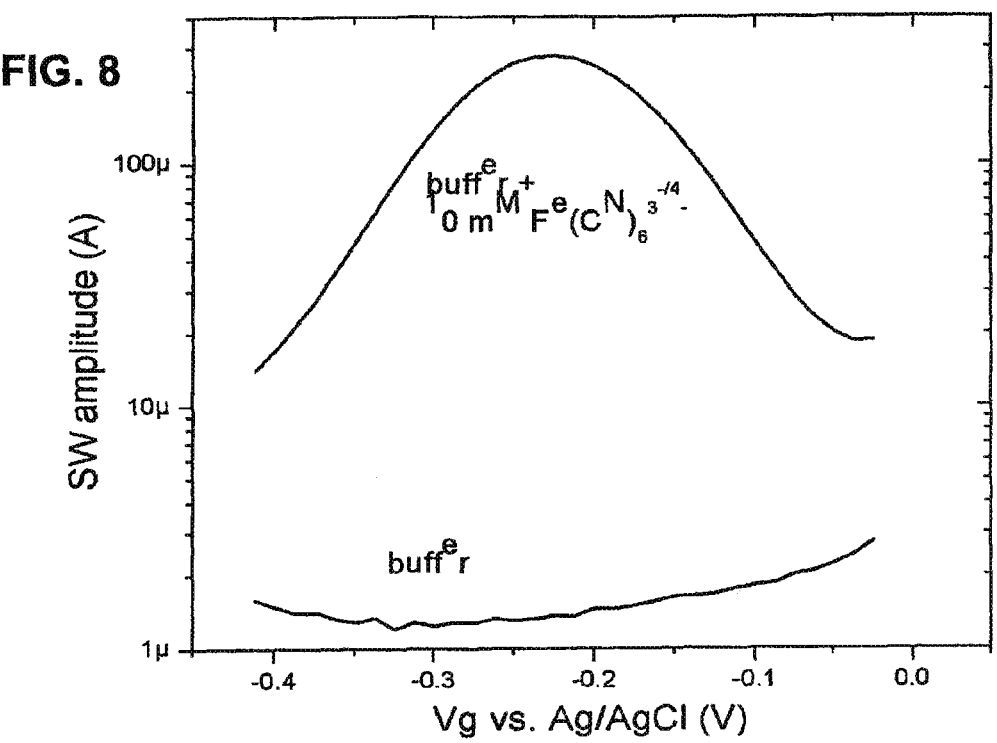
FIG. 8 shows an example of square wave voltammetry (SWV) response of a nanotube electrode such as shown in FIG. 7, illustrating the effect of a ferrocyanide/ferricyanide redox couple.

FIG. 8 shows an example of square wave voltammetry (SWV) response of a nanotube electrode such as shown in FIG. 7 in buffer alone (lower curve), as compared with the response in a buffer with added redox couple (upper curve). In this example, the redox couple includes 10 mM solution of $Fe(CN)_6^{3-/4-}$ added to AP buffer. As it can be seen from FIG. 2, the ferrocyanide/ferricyanide redox couple produces more than 100 fold increase of electron transfer between solution and the device as indicated by square voltammetry method. The device shows purely electrochemically capacitive behavior in buffer alone, but converts to 'resistor' in the presence of ferrocyanide/ferricyanide redox couple. Square voltammetry methods are further described in A J Bard and L Faulkner, *Electrochemical Methods: Fundamentals and Applications* (Wiley and Sons, New York, 2001); and J Wang, Analytical Electrochemistry (Wiley and Sons, New York, 2000), which publications are incorporated by reference.

Figure 9:
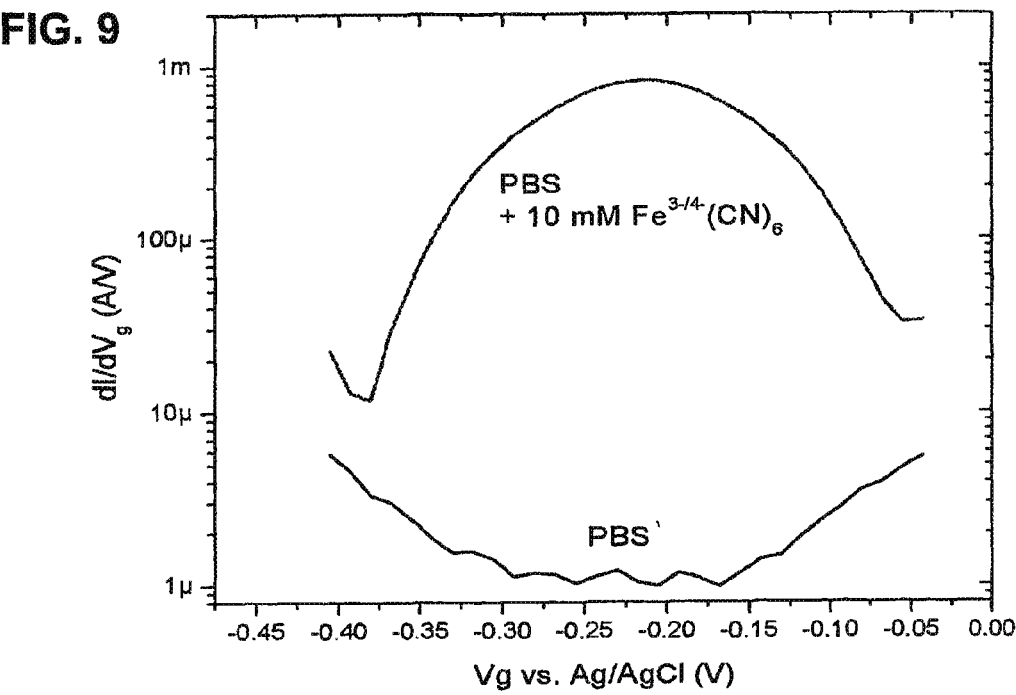
FIG. 9 shows an example of differentiating cyclic voltagrams (CV) illustrating the response of a nanotube electrode such as shown in FIG. 7 with a ferrocyanide/ferricyanide redox couple.

As shown in FIG. 9, further amplification of the dynamic range can be achieved by differentiating cyclic voltagrams (CV): The maximum of the derivative of the totally reversible system is close to the half-potential value, which happens to be around −230 mV versus Ag/AgC reference electrode. With this approach the response is extended to three orders of magnitude, comparing the response with buffer alone (lower curve) versus buffer with ferrocyanide/ferricyanide redox couple (upper curve).

In addition or in substitution to the ferrocyanide/ferricyanide redox couple described, alternative redox couple species may be employed without departing from the spirit of the invention.

Example E

Printed Substrate Sensor Device

An alternative exemplary embodiment of an electrochemical sensor include single walled carbon nanotubes (SWNTs) having aspects to the invention, configured in one example as a test strip for detection of glucose.

FIG. 10, Views A-C illustrate an exemplary electrochemical sensor 40, in this example configured as a blood test strip. A first substrate 41a (View A) and a second substrate 41b (View B) comprise a flexible sheet material such as PET polymer. A counter electrode 42 (preferably comprising a conductive ink) is printed, screen printed, shadow masked, or otherwise deposited on substrate 41a. Additional optional electrodes such reference electrode 43 and/or calibration electrode 44 may be deposited adjacent counter electrode 42. A conductive nanostructured film electrode 45 is deposited on substrate 41b. Film 45 may be printed, or may be spray deposited in the manner described with respect to the sensor 20 of FIG. 4A.

Substrates 41a and 41b are preferably shaped so that they may be counter-posed and attached to one-another, such as by adhesive layer 46 to form a multilayer assembly (View A+B). Adhesive layer 46 may serve as an insulator to electrically isolate the counter electrode 42 (and also 43-44) from nanotube film 45 in the assembly, and the adhesive may also serve as a space to maintain a space between the substrate layers 41a-41b (best seen in cross-section View C). A gap or space in the adhesive layer 46 adjacent one end or other portion of the substrates 41 may serve to create sample well 47, comprising a void between the layers, the well 47 communicating with one or more sample ports 49 (in this example, ports 48a, 48b in the sides of sensor strip 40). Additional functionalization material 49 (e.g., comprising GOx for an exemplary glucose detector) may be deposited on either or both of electrode 42 and/or film 45 in line with sample well 47.

As seen in FIG. 10, View C (detail), a blood sample 11 may be drawn by capillary action into sample well 47 so as to contact both counter electrode 42 and film 45, and so as to dissolve associated functionalization 49. A signal (e.g., an electrochemically generated current) is measured by monitor circuitry 50 (diagrammatically indicated by a meter), so as to produce a measurement of the glucose concentration (or other target analyte) in sample 11.

Advantageously, the nanotube film 45 may be pre-functionalized or to deposition with nanoscale Pt particles. For example, surface oxidized SWNTs may be suspended (e.g., with sonification) in a solvent such as ethylene glycol-water mixture, containing a selected concentration of hexachloroplatinic acid Preferably, the pH is adjusted (e.g. with NaOH) to about 13. The solution may be heated to about 140 deg. C. in an oxygen-free atmosphere for an period to permit Pt reduction. The treated SWNTs may be centrifuged to remove solvent, and re-suspended in a desired deposition solvent prior to applying to substrate 41b. The concentrations of reagents and treatment temperature and time may be adjusted to produce the desired Pt content in the final film.

The conductive nanostructured film electrode 45 preferably comprise a film of carbon nanotubes, and more preferably comprises a highly-uniform network of SWNTs. In comparison to conventional glucose test strips (e.g., the Freestyle™ system, and others) employing other conductive materials, the film 45 is configured to provide at least the following advantages:

(a) Accelerated response of sensor 40 to sample 11—film 45 provides a faster electrochemical response signal to reaction products (e.g., hydrogen peroxide and gluconic acid) from the enzymatic reaction to the glucose substrate.

(b) Film 45 provides a smooth, consistent surface for binding GOx (or other catalysts or cofactors), so as to produce a test strip with more consistent response to samples, so as to greatly reduce system calibration problems, leading to reduced costs, improved reliability and greater convenience of use.

The inclusion of platinum or Pt (or other metal catalyst) in the conductive nanostructured film electrode 45 is preferably as nanoscale particles of a size generally on the order of the diameter of the nanotubes or smaller. In comparison to a film 45 without Pt functionalization, the Pt containing; film provide at least the following advantages:

(a) The Pt nanoparticles provide an even faster electrochemical response signal to reaction products (e.g., hydrogen peroxide and gluconic acid).

(b) The Pt nanoparticles provide an even better binding point for immobilizing GOx (or other catalysts or cofactors), so as to advantageously produce a test strip with more consistent response to samples.

(c) The described process for pre-functionalizing the nanotubes with Pt (or other metal catalyst) permits convenient fabrication and a much more advantageous control of Pt particle size, distribution and content than other methods of applying or depositing Pt to a previously formed nanotube network, thus improving the value of (a) and (b) above.

Example F

SWNT-PAWS Functionalization

In this exemplary embodiment, the nanotubes are treated with a polymeric functionalization material. In this novel embodiment, the functionalization material includes poly (m-aminobenzene sulfonic acid) or PABS covalently attached to SWNTs (SWNT-PABS). The functionalized nanotubes may be included in any of the suitable sensor embodiments having aspects of the invention, such as the sensors described and shown in FIG. 2A, FIGS. 4A-C, and FIG. 10. In this example, the PABS-functionalized nanotubes were included in an electrochemical test strip generally similar to that shown in FIG. 10.

A composition of SWNT-PABS powder is commercially available from Carbon Solutions, Inc. of Riverside Calif., and may be made as described in B Zhao et al, "Synthesis and Properties of a Water-Soluble Single-Walled Carbon Nanotube Poly(m-aminobenzene sulfonic acid) Graft Copolymer", Adv Funct Mater (2004) Vol 14, No 1 pp 71-76, which article is incorporated by reference. An aqueous solution of SWNT-PABS may be prepared by ultrasonication (e.g., 1 mg/mL). After brief sonication, a homogeneous dispersion of carbon nanotubes was obtained.

The sensor in this example includes a flexible substrate comprising PET sheet (which are commercially available from McMaster-Carr Supply Company of Chicago Ill.). The carbon nanotubes dispersion was sprayed with an air brush in several steps with intermediate drying until the desired resistance was obtained. In this example, the deposition was carried out on with the substrate on a hot-plate with the temperature of about 75 degree C., and the dispersion was deposited step-wise until the half-inch resistance obtained using the pin probe reached a target resistance (for example, from about 1 to about 15 K Ohm).

The response of the sensors to glucose was demonstrated using the H2O2 solution as a simulant to glucose (note that the reaction of GOx with blood glucose produces peroxide, which in turn generates the measurement current). The 2.5 mM H2O2 solution was prepared corresponding to the 400 mg/dl of glucose concentration. A meter from Hypogard was used to record the reading of the glucose. The meter was calibrated based on the conductivity of CNT film.

The response of PABS-SWNT strip sensor to 400 mg/dl glucose is as shown in FIG. 11. The meter records 367 mg/dl giving less than 10% error in the measurement of actual glucose concentration. Also the time (<2 seconds) required for measurement is less than in a conventional test strip, demonstrating that the exemplary sensor is a faster sensor for 'glucose detection.

The molecular sensing mechanism of glucose for the SWNT-PABS can be understood considering the chemistry of polyaniline (PANI). PANIs are appealing for sensor applications because their electronic properties can be reversibly controlled by doping/dedoping at room temperature. The chemical modification of SWNTs significantly affected the sensitivity and reversibility of the behavior of the sensors. PABS is a water-soluble conducting polymer. The presence of SO3H groups improved the solubility and processability of this sulfonated polyaniline derivative, and it is especially attractive for introducing acid-base sensitivity together with a further doping response into sensor devices.

Glucose chemically binds to the benzene sulfonic acid groups, which greatly influences the electrochemical activity of the polyaniline backbone due to steric effects. The carbon nanotubes in the composite not only increase the effective electrode surface area (thereby increasing the density of benzene sulfonic acid groups for glucose binding), they also greatly increase the stability of the film.

In this concept, the conducting polymer (PABS) acts as the immobilization matrix as well the physio-chemical transducer to convert a chemical signal (change of chemical potential of the microenvironment) into an electrical signal. The conducting polymer acts as the electron mediator while the carbon nanotubes provide enhanced surface area.

The sensors in this example may be made from pre-functionalized nanotubes, thus eliminating an additional step to functionalize nanotubes with polymers. Unlike conventional glucose biosensors, no electrochemical deposition is required in this case making it easy-to-fabricate sensor process.

Alternative techniques may be employed to functionalize nanotubes with other suitable conductive polymeric materials, such as PANI or may be employed. See, for example, the electrochemical treatments described in T Zhang et al, "Nanonose: Electrochemically Functionalized Single-Walled Carbon Nanotube Gas Sensor Array", Proc. 208th Meeting of Electrochemical Society (Los Angeles, Calif. Oct. 16-21, 2005), which is incorporated by reference. Similarly, different polymer like poly (aniline boronic acid); various functionalized tubes can also be used to functionalize CNTs for non-enzymatic glucose detection.

The SWNTs (or alternative nanostructures) functionalized with PABS (other alternative conductive polymers such as other polyaniline derivatives) are advantageously employed to comprise the nanostructured film electrode 45 as shown in FIG. 10. In comparison to conventional glucose test strips (e.g., the FreeStyle™ system, and others) employing other conductive materials, the film 45 comprising is configured to provide at least the following advantages:

(a) The example electrode film 45 having conductive polymer functionalization (e.g., PARS) provides a faster electrochemical response signal to reaction products (e.g., hydrogen peroxide and gluconic acid) from the enzymatic reaction to the glucose substrate. In addition, where, as in this example, there is a covalent bend between the conductive polymer (e.g., PABS) and the conductive nanostructure (e.g., SWNTs), the accelerated response is particularly notable.

(b) The example electrode film 45 having conductive polymer functionalization provides a smooth, consistent surface for binding GOx (or other catalysts or cofactors), providing the advantageous described above with respect to Pt functionalized nanotube films.

(c) In many cases, the example electrode film having conductive polymer functionalization of this EXAMPLE E provides better sensor properties and response, in comparison to the alternative film having Pt functionalization as described in EXAMPLE E (d) An additional alternative electrode film 45 may advantageously have conductive polymer functionalization in combination with Pt functionalization. For example, SWNTs (or other nanostructures) may be pre-functionalized with both PABS and Pt, and then deposited as a film electrode. In yet other alternative examples, a film electrode may be deposited from a mixture of differently-functionalized nanotubes (e.g. SWNT/PABS+ SWNT/Pt); or a film electrode may be deposited in layers (e.g., stepwise deposition) of differently-functionalized nanotubes (e.g. SWNT/PABS layered with SWNT/Pt).

Example G

Capillary Strip with CNT Working Electrode

FIGS. 12A-12B illustrate an exemplary electrochemical test strip 50 having a CNT working electrode 55 and a sample volume 56 communicating with a capillary vent 57. Substrate 51 (e.g., PET) supports a pair of traces 52a, 52b which lead sample volume enclosure 56.

The working electrode comprises, for example, a conducting carbon path with CNTs deposited on top of it. Traces 52a, 52b communicate with working electrode 55 and counter electrode 58, which are exposed within sample volume enclosure 56. In this example, sample volume enclosure 56 may be formed by a layer of insulating material 53 which serves to: enclose the sides of volume 56; electrically isolate traces 52a, 52b, and define a capillary entrance 59 at the tip or margin of strip 50.

The upper bound of sample volume 56 is formed by plate 60 (e.g., a thin plastic piece on the active electrode area using a pressure sensitive adhesive), which includes a downstream capillary vent 57.

Although trace 52a and working electrode 55 may be integral, conveniently trance 52a may comprise screen-printed Ag and electrode 55 may comprise printed carbon. A layer including a CNT network is deposited on the surface of electrode 55.

Preferably, trance 52b comprises screen-printed Ag and counter/reference electrode 58 comprises a Ag and AgCl mixture. Traces 52a, 5211; may alternatively comprise suitable conductive materials.

An analyte-selective redox enzyme (and suitable cofactors and/or mediators) are deposited on or adjacent working electrode 55. Alternatively or additionally, enzyme and CNTs may be deposited simultaneously to form the surface layer of electrode 55

A sample, such as a droplet of blood, is applied to entrance 59, where it moves by capillary forces to fill volume 56. Suitable circuitry (not shown) detects an analyte via a signal transmitted via traces 52a, 52b (amperometric, coulometric, or the like).

Carbon Nanotubes (CNTs) Application

Carboxylic acid functionalized CNTs may be suspended in water by sonicating the mixture for about 1 hour or more. The concentration of CNT may be about 0.1 mg/ml. The concentration and sonication time depends on the type of CNTs and solvents. The next step is to put this suspension on the carbon conducting layer to form the working electrode 55. For example, this may be performed using the moving head type BioDot instrument. About 40 nl of the CNT suspension drops may be cast on the electrode in one cycle of the instrument. This may be repeated with small changes in spacing until the desired CNT amount and extent of coverage is obtained on the electrode.

Example H

Further Improvements and Aspects of the Invention

Carbon Nanotubes Enabled Improved Accuracy of Biosensors

Biosensors used for monitoring analytes such as glucose in real samples such as blood are susceptible to interferences from other species e.g. ascorbic acid, uric acid, other saccharides such as galactose etc. likely to be present in the sample. Additionally, depending on the enzyme and mediator used oxygen dependence could also arise. Hematocrit, which is the amount of red blood cells in the sample may also influence the glucose measurement. These interfering factors adversely affect the accuracy of glucose measurement.

Various methods may be employed to increase the accuracy of glucose monitoring. Using an electro-catalyst such as carbon nanotubes (CNT) to lower the voltage of glucose detection may be used to eliminate some of these interferences. In addition the faster reaction may reduce the hematocrit and oxygen sensitivity. Alternatively, hematocrit sensitivity may be addressed, in particular, by measuring the hematocrit by some other method such as Electrochemical Impedance Spectroscopy (EIS) and initial glucose concentration by electrochemical measurement and then estimating the corrected glucose concentration based on these two measurements based on a calibration algorithm.

One aspect of the invention includes the use of CNTs to improve the hematocrit estimation using a technique such as EIS and the glucose measurement using amperometry/coulometry resulting in an overall accuracy better than that can be achieved without using CNTs. CNTs have high surface area and according to various embodiments have various functionalization chemistries. In combination with a suitable enzyme-mediator system CNTs provide a highly accurate sensor in the following way:

Various parameters such as phase shift and impedance can be measured for determining the hematocrit levels at one or different frequencies of the AC waveforms varying in voltage, set up for the particular enzyme-mediator system.

The hematocrit estimation can be done by AC measurement while the glucose detection may be performed at a fixed potential.

For an effective measurement of hematocrit it is useful to have a good dependence of phase shift and or magnitude of impedance on hematocrit concentration.

It is also desirable to have as accurate as possible early glucose estimation at a low potential, which can be further corrected for hematocrit bias. This depends on the mediator-enzyme system; in one example, potassium ferricyanide-glucose oxidase system is at 300 mV vs AgCl or less.

CNT have high surface area and may have various functionalization chemistries. Different hydrophobic/hydrophilic behavior is tailored to achieve good hematocrit dependence by EIS at particular frequencies. This combined with the CNT enables fast reaction of the mediator. Consequently inherently low hematocrit dependence results in an insensitivity to a wide range of hematocrit (packed cell volume) values.

CNT-based sensors having a enzyme-mediator chemistry, are particularly useful for measuring glucose in neonates who have high hematocrit (55%-65%) concentration and whose hypoglycemic limit is lower than for adults (40 mg/dl as opposed to 60 mg/dl), wherein high inaccuracies may result using conventional glucose sensors.

Carbon Nanotubes—FAD-GDH Enzyme Based Sensor

One aspect of the invention provides improved electrochemical performance using carbon nanotubes (CNTs) and heme containing dehydrogenase enzymes such as glucose dehydrogenase (GDH) along with a suitable mediator for glucose monitoring.

Advantages of using FAD-GDH include good stability, higher substrate specificity and oxygen insensitivity.

Direct electron transfer between FAD and an electrode using CNTs as molecular wires provides a mediator-free sensor if desired. The electrocatalytic nature of carbon nanotubes provides improved electrochemistry—higher current at low potential, higher reversibility as shown by reduced peak separation, for a redox mediator such as potassium ferricyanide using CNT. Combining all the advantages of CNT for the mediator (e.g., ferricyanide), the enzyme with the above-mentioned advantages of FADGDH provides an excellent biosensor with the advantages described herein.

Improved Sensor Performance using CNTs with Electro-Catalysts such as Metals

Carbon nanotubes (CNTs) have unique electronic and topological properties. One aspect of the invention provides improved electrochemical performance of CNT modified electrodes for various analytes such as $H_2O_2$, Potassium ferricyanide, NADH and as wells as others such as PQQ, osmium complex etc. Monitoring these compounds is very important for biosensor applications such as glucose monitoring. This is because these compounds are used as mediators, co-factors or analytes and are the targets of detection for glucose monitoring. The analytical utility of the improved electrochemical performance includes:

lower applied potentials and higher signal
lower interferences
better electrode surface morphology—CNTs are nanometer in size as compared to micron sized carbon particles used in screen printed electrodes. This along with the electrocatalytic activity of CNTs generating higher signals enables obtaining a more reproducible biosensor.
better accuracy in the low ranges of glucose concentration
more consistent electrochemical responses enabled by better surface morphology and electrocatalytic activity
decreased hematocrit and oxygen dependence
direct electron transfer between the enzyme and electrode Aspects of the invention provide enhancement in the electrochemical performance that can be achieved by using CNTs, which can be increased further by using another electro-catalyst such as (but not limited to) metals or metal oxides. Alternative electrocatalyst may include metals/metal derivatives such as Pt, Pd, Au, $Fe_2O_3$, and the like which will be apparent to ones skilled in the art. Such electro-catalysts can be deposited on a CNT-modified electrode by techniques such as sputter coating, electrochemical methods, e.g. by reducing the corresponding metal salts or simply by suspending the compound in a solvent and casting it on the electrode to achieve deposition of particles of various dimensions. Alternatively CNTs can be deposited on the electro-catalyst modified electrode. See for example, U.S. application Ser. No. 10/945,803 filed Sep. 20, 2004 entitled "Multiple nanoparticles electrodeposited on nanostructures" (published 2005-0157445), which is incorporated by reference.

The advantages of using the additional electro-catalyst in a CNT-based sensor include:

Synergistic effect between CNT and the other electro-catalyst resulting in performance better than the individual components Commercial availability a low cost of a metal/metal oxide/other electrocatalyst based electrode and further enhancement can be realized by combining it with CNT with manufacturing simplicity.

Savings in materials cost.

The morphology of the electrode can be modified by appropriate placement of CNTs on the electrode, realizing other advantages such as faster response, easy diffusion of the analytes, better stability, reduced leaching for continuous monitoring etc.

If other techniques are used for determining the effect of interferences such as ascorbic acid, hematrocrits, etc. combined with the electrochemical glucose measurement, improvement can be realized in those measurements too, the result being better accuracy.

Advantages are realized with various mediator-enzyme systems depending on the interaction of CNTs and the electrocatalyst with the system. The systems may be (but not limited to) those using glucose dehydrogenase-PQQ and NAD dependent, glucose oxidase and mediators such as ferricyanide, osmium based mediators and others.

A glucose sensor using CNT with an osmium-based mediator and pyrroloquinoline quinone (PQQ) and glucose dehydrogenase enzyme (GDH) Aspects of the invention provide a biosensor including an osmium polymer based mediator e.g. osmium poly (pyridyl) derivative and the enzyme pyrroloquinoline quinone (PQQ)-glucose dehydrogenase (GDH).

See additional description in U.S. Pat. No. 7,052,591 entitled "Electrodeposition of redox polymers and co-electrodeposition of enzymes by coordinative crosslinking"; and US Patent Publication 2006-0169599 entitled "Small Volume In Vitro Analyte Sensor," each of which are incorporated by reference.

This unique system combines highly desirable attributes of CNTs, PQQ-GDH and osmium complex with the following advantages:

Direct electron transfer between the enzyme and CNT combined with the highly efficient osmium based mediator.

Very high sensitivity, high signal to noise ratio, lower applied potentials and higher signal, lower interferences, better electrode surface morphology, better accuracy in the low ranges, more consistent electrochemical responses, decreased hematocrit and oxygen dependence, faster response, reduced calibration code requirements etc. The redox behavior of PQQ is improved by CNT The electron transfer ability of the osmium based mediator may be improved by the use of CNTs.

CNTs functionalized with different chemistries and suspended in different solvents influence the interaction of CNT with osmium based mediator and PQQ-GDH, the optimum combination depends on the particular electrode design, types of ink, method of measurement such as amperometric or coloumetric etc. and may be optimized for manufacturing.

The CNTs may be mixed with the mediator and enzyme or deposited sequentially for manufacturing simplicity—CNT followed by the mediator followed by the enzyme or any combination thereof or the CNTs may be covalently attached to the enzyme using chemistry such as the carbodiimide chemistry.

Method of Enzyme Immobilization for Sensor Application.

Aspects of the invention provide a method of preparation of a stable suspension of functionalized carbon nanotubes (CNT) in water aided by sonication, with addition of the enzyme glucose oxidase to the suspension and deposition of the suspension on a substrate, such as a polymer substrate with screen-printed Ag/AgCl electrodes, so as to form an electrochemical sensor for monitoring of d-glucose in whole blood.

Other alternatives include using an electron transfer mediator such as Pt nanoparticles, ferrocence etc. deposited along with the working electrode followed by enzyme immobilization. This leads to a multi step process and can contribute to the problem with precision of the electrodes. Due to the use of hydrophilic CNT functionalization, aqueous dispersion of CNT is convenient. This enables the incorporation of enzyme in the suspension. This one step process avoids solvents or binders which are not compatible with enzymes. The new method described reduces cost and improve precision of measurement.

Advantages of the inventive enzyme immobilization method include single step deposition of carbon nanotubes (electrode material) and the enzyme (or other functional biomolecule) on the sensor surface. The enzyme retains its activity and stability after immobilization on the electrode. In certain embodiments, depositing the biomolecule and carbon nanotubes together in a single step involves PABS-CNT chemistry used for the functionalization of CNTs.

This method leads to a decrease in the number of steps for the sensor fabrication which improves reproducibility and improves precision in the manufacture of glucose strips on a commercial scale. Other advantages include improved stability of the CNT suspension (due to the biomolecule-nanotube interaction), reduced mass transport limitation for the oxidation of enzymatically generated hydrogen peroxide, better chance of direct electron transfer between the CNT electrode and the enzyme (due to the positioning of CNTs within the tunneling distance of the cofactors). This can make the sensor more sensitive, selective and faster responding.

Various combinations/variables and more general applications that are covered under this application:

Types of carbon nanotubes: processed single walled nanotubes (SWNT) containing carbonaceous and catalyst related impurities such as the metal/metal oxide and other materials remaining from manufacturing, carboxylic acid functionalized SWNT, poly (m-aminobenzene sulfonic acid) or PABS functionalized SWNT and pristine as well as carboxylic acid functionalized multiwalled carbon nanotubes (MWNT) can be used along with the enzyme. Functionalization chemistries may be used to facilitate solubilization of the CNTs in water. These include carboxylic acid, PABS, and other hydrophilic chemistries. In other embodiments, pristine (no functionalization) SWNTs and MWNTs are used. Using pristine nanotubes in embodiments wherein attachment of the biomolecule alone is sufficient to solubilize the nanotubes simplifies the manufacturing process. For example, proteins such as streptavidin, different antibodies or antibody fragments, peptides, glycans, carbohydrates, aptamers, nucleic acids—example single stranded deoxyribonucleic acid (DNA) may be sonicated with pristine nanotubes to prepare the suspension. In other embodiments, a solubilization chemistry is necessary to achieve desired suspension.

Process of preparing the suspension: In certain embodiments, the methods involve sonication of the (CNT+ enzyme) together. In other embodiments, the methods involve sonication of CNT first, and the enzyme added later (for example, if prolonged sonication causes the enzyme to denature) with or without further sonication to disperse the biomolecule. In other embodiments, the CNT is suspended in a suitable buffer, for example, if the enzyme will denature in water. In certain embodiments, one or more other forms of mixing, stirring, vortexing etc. may be used in addition to or instead of sonication.

Immobilization method for the mixture—using BioDot's BioJet Plus instrument (moving head type): using the BioJet (spray) along with shadow mask to cover appropriate areas; using the BioDot option (drop casting). Other methods include screen printing, piezoelectric methods and dip coating.

Types of biomolecules: as indicated above, the functionalized biomolecule is attached to the CNTs to interact with the analyte. In addition to enzymes (with or without mediators) that interact with glucose (e.g., glucose oxidase), this method is applicable to various enzymes such as horseradish peroxidase and other oxido-reductase enzymes for incorporation in sensing devices. Other functional biomolecules that may be immobilized using the methods described herein include antibodies and nucleic acids. Specific examples include proteins such as streptavidin, different antibodies or antibody fragments, peptides, aptamers, DNA and RNA Different feature sizes (width, pitch and thickness) of the electrodes which determine the microstructure of the conducting paths can be fabricated using the method described here.

Various substrates for deposition—Polyethylene terephthalate, polyimide, alumina ceramic, polycarbonate etc. In certain embodiments, there may be a silver contact layer underneath the CNT layer.

According to various embodiments, the methods may be used to make sensors as described above, e.g., with a 2 or 3 electrode configuration (a separate counter electrode or not).

In depositing the CNT-biomolecule, the CNTs may be randomly sprayed or aligned.

During sonication, the biomolecules attach to the CNTs, thereby solubilizing them and allowing them to form a stable solution that may be deposited on the electrode surface. Without solubilization, the hydrophobic CNTs are not suspended within the solution and will settle down at the bottom of the vial or other container. By attaching the biomolecules the CNTs disperse throughout the solution, ready for deposition on the electrode surface. Depending on the particular biomolecule, attachment may involve non-covalent interaction, covalent bonding, hydrophobic interaction, and It stacking. For example, DNA attaches to the nanotubes via n bonding. Proteins such as bovine serum albumin (BSA), streptavidin, glucose oxidase, etc. attach via non-covalent electrostatic/hydrophobic interaction with the nanotubes. In this manner, the CNTs are solubilized and bio-functionalized for interaction with the analyte in a single step. The resulting suspension is stable, i.e., the CNTs do not fall out of the suspension. Suspensions of enzyme-CNT conjugates have been demonstrated to be stable for at least up to a week. The CNT-biomolecule conjugates remain intact during the deposition onto the electrode, providing bio-functionalized CNTs on the electrode.

In certain embodiments, a separation operation (e.g., centrifugation, decantation, dialysis, filtration, gel chromatography) is performed between the sonication and deposition operations, to separate unattached and loosely attached biomolecules and CNTs from the stable suspension. In other embodiments, no separation operation is required or performed between these operations, further simplifying the method. Relatively low concentrations of CNTs facilitate the suspension being deposition-ready after sonication; in certain embodiments, the concentration of CNTs in solution is between about 0.01 mg/ml-1 mg/ml, or 0.1-1 mg/ml, e.g., 0.1 mg/ml.

Application of disposable sensors for self monitoring of glucose is important due to the frequent use of strips required and the growing number of diabetics. The greater control of surface morphology afforded by the use of nanotubes combined with the one step process of enzyme immobilization could significantly improve the precision of the electrodes manufactured on a commercial scale. The one step process could also lead to an easier fabrication process and save manufacturing costs. Improved sensitivity, a faster response, and selectivity against interferences such as due to ascorbic acid, uric acid could lead to greatly improved and consistent performance at a lower cost.

Reduced Oxygen and Hematocrit Bias for Glucose Sensors Using Carbon Nanotubes

Variation in response due to the change in the levels of hematocrit and oxygen is an important consideration for biosensors used to monitor substances in whole blood such as sensors for glucose monitoring. This is not well understood in the prior art, see US Patent Application 2004-0079,653 entitled "Biosensor having improved hematocrit and oxygen biases", which is incorporated by reference.

Hematocrit bias can be caused by a variety of factors, system specific, such as:

Volume exclusion—higher level of hematocrit, artificially lower sensor response
Decreased diffusion of the analyte
Increased solution resistance
A reaction going to completion utilizing all the analyte in the sample, decreases hematocrit sensitivity
Slow reaction rate of the mediator may be responsible for significant hematocrit sensitivity.

Oxygen bias (capillary, venous, arterial blood sample) is caused for the following reasons:

For enzymes such as glucose oxidase—oxygen is a co-substrate
For enzymes such as glucose dehydrogenase (GDH), which are not oxygen dependent, this bias can be caused by the slow mediator reaction. The slow reaction increases the susceptibility of the intermediates to oxygen quenching. It depends on the type of enzyme and mediator.

Aspects of the invention include embodiments in which catalytic activity and greatly improved electrochemical behavior of carbon nanotubes provides advantages for important compounds including hydrogen peroxide and redox mediators such as potassium ferricyanide. The faster electron transfer and redox behavior of these molecules with CNT provides a method of improved hematocrit and oxygen bias reduction using CNT for sensors, such as using nicotinamide adenine dinucleotide (NAD'), pyrroloquinoline quinone (PQQ), as the cofactors/coenzymes or having an active site such as FAD and various mediators such as osmium complex, 1,10-phenanthroline quinone (PQ), potassium ferricyanide or others.

In addition the porous structure of CNT film and its interaction with the enzyme may improve the diffusion of the analyte to the enzyme and the electrical communication between the enzyme cofactor and the electrode further reducing the hematocrit and oxygen bias.

EXPERIMENTAL

The following provides details illustrating aspects of the present invention. These experimental examples are provided to exemplify and more clearly illustrate these aspects of the invention and are in no way intended to be limiting.

Another advantage to the CNT sensors described above over conventional (non-CNT) sensors is reduced sensor-to-sensor variation. The below table contains data showing reduced variation (as indicated by lower coefficient of variation (% CV)) with CNTs deposited on screen printed electrodes. Method of analysis was based on capacitance measurement in PBS by alternating current (AC) techniques.

|  | Control, n = 20 | CNT sensors, n = 20 | | |
|---|---|---|---|---|
|  |  | Formulation A | Formulation B | Formulation C |
| Average (F) | 9.29E−09 | 4.20E−06 | 5.18E−06 | 4.26E−06 |
| SD | 2.83E−10 | 8.03E−08 | 6.42E−08 | 5.80E−08 |
| CV % | 3.05% | 1.91% | 1.24% | 1.36% |

The control sensor was sensor without CNTs. As can be seen, the variation across the 20 sensors is less than 2% for each of the CNT sensors, as compared to over 3% for the control.

Figure 13:
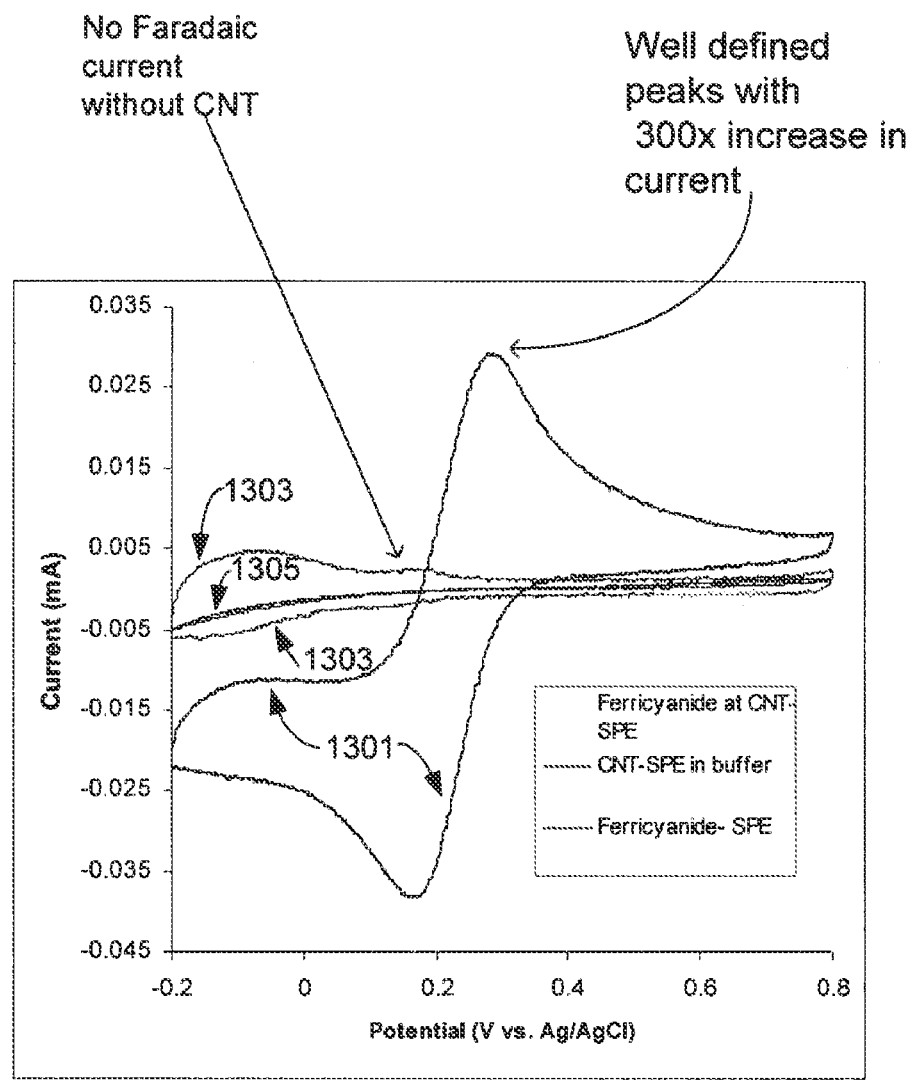
FIG. 13 is a plot showing cyclic voltammmetry data for strips ha ing CNT-functionalized conductive carbon layer and strips ha ing a conductive carbon layer without CNTs.

FIG. 13 shows cyclic voltammmetry data with 10 mM potassium ferricyanide for strips having CNT-functionalized conductive carbon layer and strips having a conductive carbon layer without CNTs. (Supporting electrolyte-50 mM pH 7.4 phosphate buffer+0.1 m KCl, scan rate 100 mV/sec, 10 mM potassium ferricyanide. Experimental set up—Cyclic voltammetry (CV) with standard three electrode electrochemical cell, Working electrode—screen printed electrode with and without CNT functionalization, Ag/AgCL reference electrode, Pt wire counter electrode.)

No electrochemical signal is recorded for control strips without CNTs. (1301 shows ferricyanide at CNT-SPE (carbon nanotube-screen printed electrode); 1303 shows CNT-SPE alone; and 1305 shows ferricyanide (no CNTs). FIG. 13 shows that highly enhanced electrochemical performance is obtained with CNT functionalized conductive carbon layer.

Figure 14A:
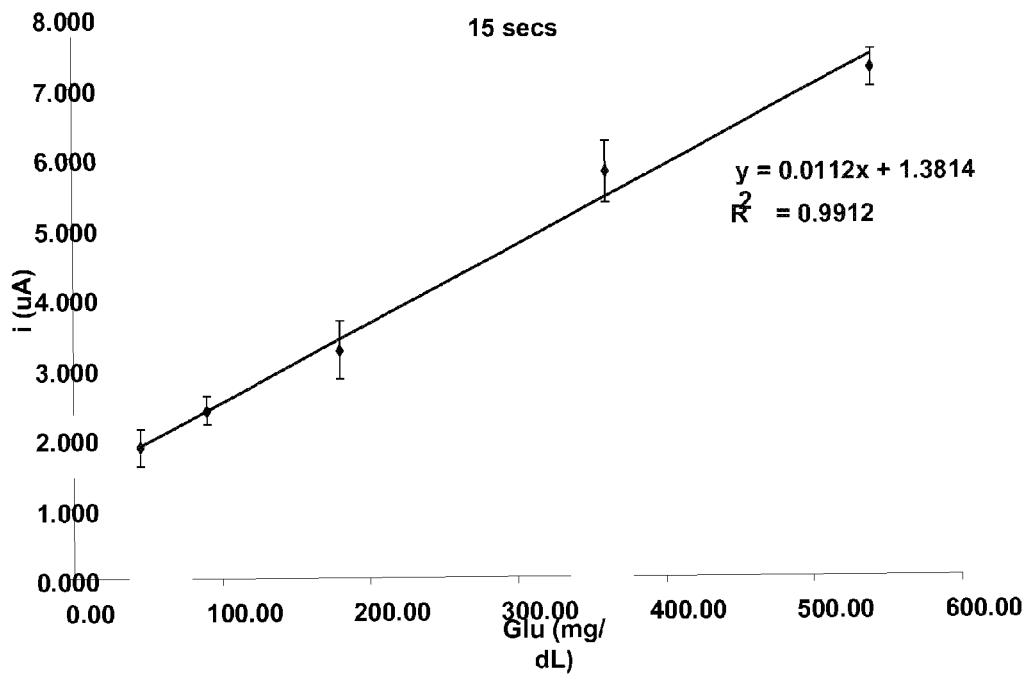
FIG. 14A is a plot showing glucose detection in blood spiked with various concentrations of glucose using glucose oxidase enzyme and potassium ferricyanide mediator with a CNTs modified electrode.

FIG. 14A shows glucose detection in blood spiked with various concentrations of glucose using glucose oxidase enzyme and potassium ferricyanide mediator with a CNTs modified electrode. Potential 300 mV vs. Ag/AgCl.

Figure 14B:
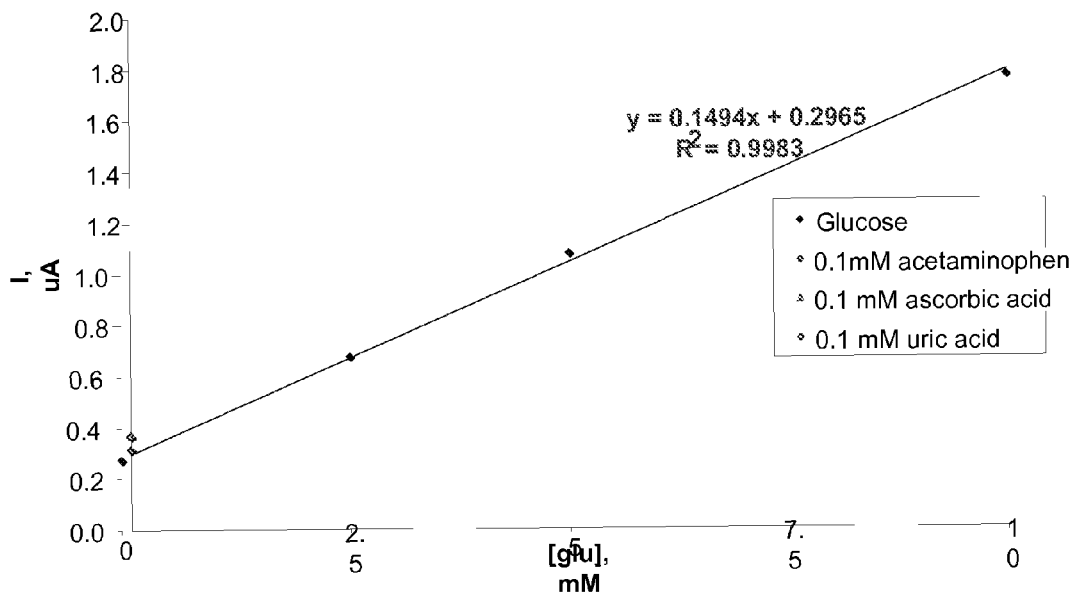
FIG. 14B shows glucose detection in PBS spiked with various concentrations of glucose using glucose oxidase enzyme and potassium ferricyanide mediator with a CNTs modified electrode.

FIG. 14B shows glucose detection in PBS spiked with various concentrations of glucose using glucose oxidase enzyme and potassium ferricyanide mediator. Potential 300 mV vs. Ag/AgCl. Enhanced electrochemistry does not increase background as seen by low signal for interfering species (ascorbic acid, acetaminophen) compared to glucose. No signal obtained without CNTs on these electrodes.

Figure 15A:
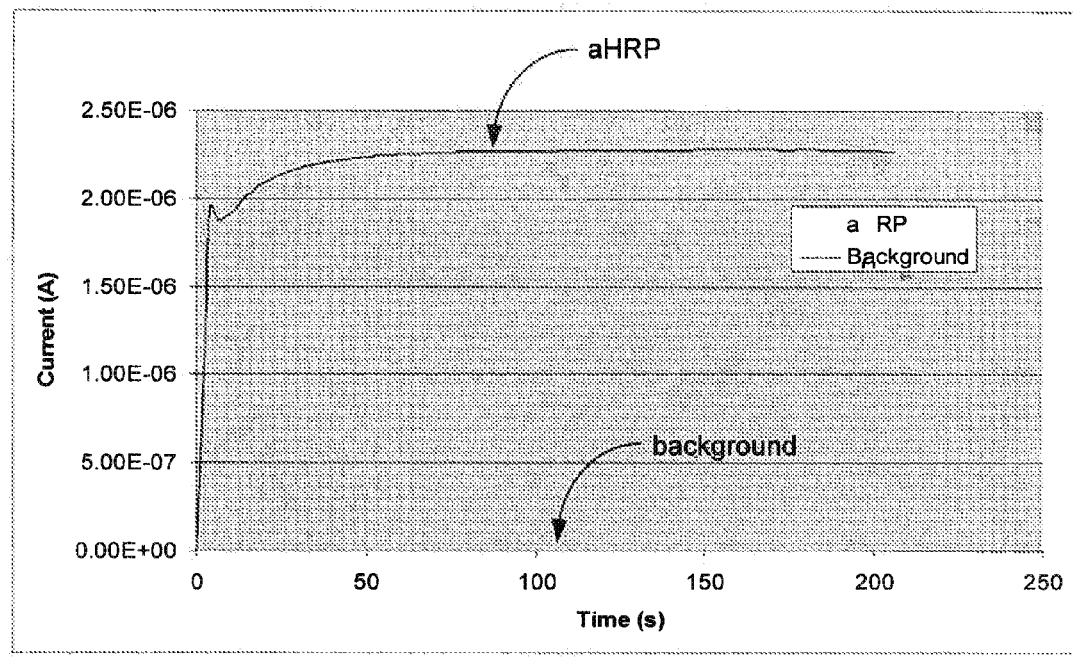
FIGS. 15A-15B are plots showing responses of electrochemical sensor embodiments functionalized with antibodies.
Figure 15B:
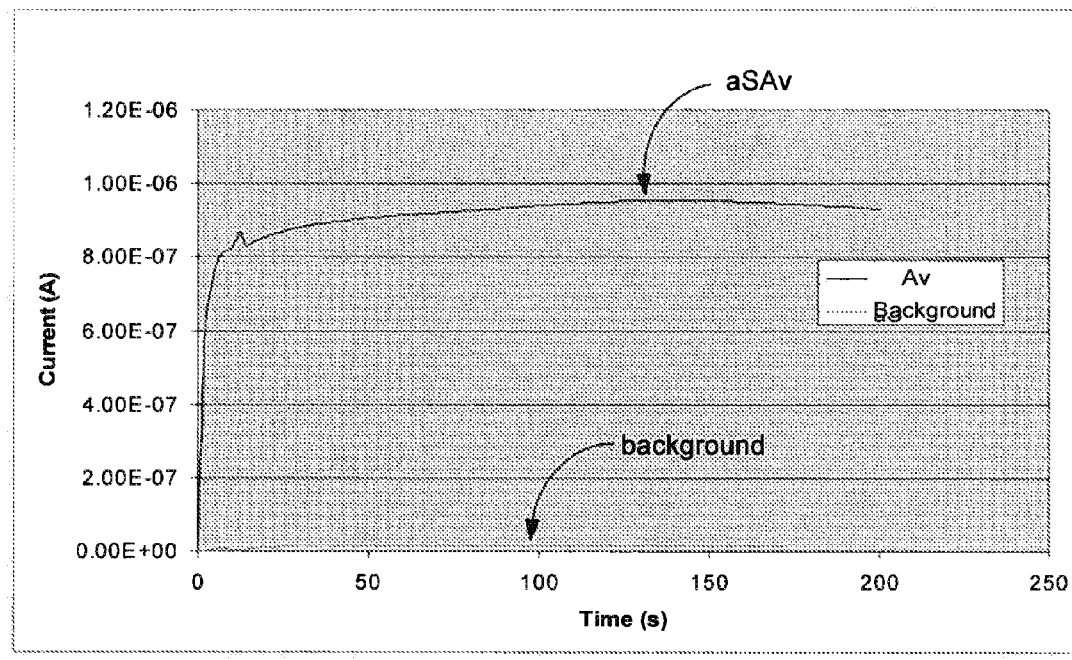

FIGS. 15A and 15B show that antibodies used to suspend pristine CNTs retain their functionality. 3 µL of 0.33 mg/mL pristine CNTs+1.5 mg/mL anti-Horseradish Peroxidase (HRP) antibody suspended in water by sonication for 60 min dropcast on a screen printed carbon electrode. Screen printed AgCl electrode was the reference electrode. The electrodes were treated with Starting Block solution from Pierce for 1 hr at room temperature to prevent non specific adsorption of the reporter HRP. For background data the bare carbon electrodes were used after blocking by a similar procedure. The reporter solution was 167 ng/mL anti Human chorionic gonadotropin ahCG-HRP (dilution from stock in starting block). FIG. 15A shows the electrochemical signal for the background and aHRP antibody-functionalized CNTs. The electrochemical signal was obtained by adding 2 ml TMBB (10% Dimethyl Sulfoxide in Phosphate Citrate Buffer+417 nM 3,3,5-tetramethyl-benzidine+10 mM NaCl) and 20.0 uL 250 mM hydrogen peroxide. Applied potential was 150 mV.

3 uL of 0.1 mg/mL pristine CNTs+0.1 mg/mL anti-streptavidin (SAv) antibody suspended in water by sonication for 60 min dropcast on a screen printed carbon electrode. Screen printed AgCl electrode was the reference electrode. The electrodes were treated with Starting Block solution from Pierce for 1 hr at room temperature to prevent non specific adsorption of the reporter SAv-HRP. For background data the bare carbon electrodes were used after blocking by a similar procedure. The reporter solution was 500 ng/mL SAv-HRP. The electrochemical signal was obtained by adding 2 ml TMBB (10% Dimethyl Sulfoxide in Phosphate Citrate Buffer+417 nM 3,3,5-tetramethyl-benzidine+10 mM NaCl) and 20.0 uL, 250 mM hydrogen peroxide. Applied potential was 150 mV. Results are shown in FIG. 15B.

The invention claimed is:

1. A method of immobilizing a biomolecule for sensing a target species on a substrate to fabricate a nanosensor device for sensing the target species, said method comprising:
   providing a plurality of carbon nanotubes and a quantity of a biomolecule configured to interact with the target species in an aqueous solution;
   dispersing the plurality of nanotubes and at least some of the quantity of the biomolecule to thereby create a stable suspension of nanotubes and biomolecules in the aqueous solution;
   providing a substrate surface having an electrode surface thereon; and
   simultaneously depositing nanotubes and biomolecules from the stable suspension to at least the electrode surface to thereby immobilize the biomolecules on the substrate.

2. The method of claim 1 wherein the immobilized biomolecules retain biological activity and stability.

3. The method of claim 1 wherein the biomolecule is an enzyme, antibody or nucleic acid.

4. The method of claim 1 wherein the biomolecule is configured to interact with glucose.

5. The method of claim 4 wherein the biomolecule is selected from the group consisting of glucose oxidase, PQQ-GDH and FAD-GDH.

6. The method of claim 1 wherein the plurality of carbon nanotubes to be dispersed are pristine.

7. The method of claim 1 wherein the plurality of carbon nanotubes are functionalized with a solubilizing chemistry.

8. The method of claim 7 wherein a solubilizing agent is selected from PABS and carboxylic acid groups.

9. The method of claim 1 wherein the nanotubes are single walled nanotubes.

10. The method of claim 1 wherein the nanotubes are multi-walled.

11. The method of claim 1 wherein dispersing the nanotubes and at least some of the quantity of biomolecule comprises sonicating the aqueous solution.

12. The method of claim 1 wherein dispersing the nanotubes and at least some of the quantity of biomolecule comprises sonicating the nanotubes in the aqueous solution prior to adding the quantity of biomolecule to the solution.

13. The method of claim 1 wherein depositing nanotubes having biomolecules comprises drop casting.

14. The method of claim 1 wherein the quantity of biomolecule configures to interact with the target species comprises a biomolecule and a mediator.

15. The method of claim 1 wherein the concentration of nanotubes in the aqueous solution is between about 0.1-1 mg/ml.

16. The method of claim 1 wherein the concentration of nanotubes in the aqueous solution is about 0.1 mg/ml.

17. The method of claim 1 wherein no separation operations are performed between the dispersing and depositing operations.

18. The method of claim 1 further comprising separating unattached or loosely attached biomolecules and carbon nanotubes from the suspension prior to deposition.

19. The method of claim 1 wherein immobilizing the biomolecule to the substrate one without the use of a binding agent.

20. A nanoelectronic sensor for glucose detection comprising:
   a non-conductive substrate;
   a counter electrode and working electrode on said substrate, said working electrode comprising a carbon conductive path and having a surface comprising a carbon nanotube network;
   a glucose-selective redox enzyme and a mediator in contact with said carbon nanotube network;
   a sample well configured for receiving a sample and contacting said sample with the glucose-selective redox enzyme.

21. The sensor of claim 20 wherein the glucose-selective redox enzyme is selected from glucose oxidase, PQQ-GDH and FAD-GDH.

22. The sensor of claim 20 wherein the mediator is selected from an osmium polymer based mediator and potassium ferricyanide.

23. The sensor of claim 20 further comprising a metal catalyst deposited on the carbon nanotube network.

24. The sensor of claim 20 wherein the carbon nanotube network includes at least one carbon nanotube that is substantially parallel to the non-conductive substrate.

25. The sensor of claim 20 wherein carbon nanotubes of the carbon nanotube network are oriented substantially parallel to the non-conductive substrate.

26. The sensor of claim 20 wherein at least one carbon nanotube of the carbon nanotube network includes a plurality of glucose-selective redox enzymes attached along the length of the at least one carbon nanotube.

* * * * *